United States Patent
Meliga et al.

(10) Patent No.: US 12,090,295 B2
(45) Date of Patent: Sep. 17, 2024

(54) MICROPROJECTION ARRAYS WITH ENHANCED SKIN PENETRATING PROPERTIES AND METHODS THEREOF

(71) Applicant: Vaxxas Pty Limited, Sydney (AU)

(72) Inventors: Stefano Meliga, West End (AU); Mark Anthony Fernance Kendall, Chelmer (AU); Robert William Goddard, Capalaba (AU)

(73) Assignee: Vaxxas Pty Limited, Sydney (AU)

( * ) Notice: Subject to any disclaimer, the term of this patent is extended or adjusted under 35 U.S.C. 154(b) by 33 days.

(21) Appl. No.: 17/241,927

(22) Filed: Apr. 27, 2021

(65) Prior Publication Data

US 2021/0244926 A1 Aug. 12, 2021

Related U.S. Application Data

(63) Continuation of application No. 15/762,913, filed as application No. PCT/AU2016/050907 on Sep. 28, 2016, now abandoned.

(Continued)

(51) Int. Cl.
*A61M 37/00* (2006.01)
*A61B 17/20* (2006.01)
*A61D 7/00* (2006.01)

(52) U.S. Cl.
CPC ....... *A61M 37/0015* (2013.01); *A61B 17/205* (2013.01); *A61D 7/00* (2013.01);

(Continued)

(58) Field of Classification Search
CPC .. A61M 2037/0023; A61M 2037/0046; A61M 2037/0053; A61M 2037/0061;
(Continued)

(56) References Cited

U.S. PATENT DOCUMENTS 2,213,830 A 9/1940 Anastasi
2,881,500 A 4/1959 Furness
(Continued)

FOREIGN PATENT DOCUMENTS

AU 2001296817 B2 5/2006
AU 2021202221 A1 5/2021
(Continued)

OTHER PUBLICATIONS

Aichele et al., "Antiviral Cytotoxic T Cell Response Induced By In Vivo Priming With A Free Synthetic Peptide," *J. Exp. Med.* 171:1815-1820, 1990.
(Continued)

*Primary Examiner* — Kevin C Sirmons
*Assistant Examiner* — Alexandra E Lalonde
(74) *Attorney, Agent, or Firm* — Seed IP Law Group LLP

(57) ABSTRACT

An apparatus for delivering an active ingredient into skin of an animal at a defined depth, the apparatus including: a microprojection array including a plurality of microprojections having a density of at least 2,000 projections per $cm^2$; and an applicator that drives the microprojection array towards the skin in use so that the microprojection array impacts on the skin with a mass-to-velocity ratio of between 0.0005 g/m/s and 0.1 g/m/s per $cm^2$.

18 Claims, 18 Drawing Sheets

Related U.S. Application Data

(60) Provisional application No. 62/233,607, filed on Sep. 28, 2015.

(52) U.S. Cl.
CPC ............... *A61M 2037/0023* (2013.01); *A61M 2037/0046* (2013.01); *A61M 2037/0061* (2013.01); *A61M 2202/30* (2013.01); *A61M 2207/00* (2013.01); *A61M 2210/04* (2013.01)

(58) Field of Classification Search
CPC .......... A61M 37/0015; A61M 2202/30; A61M 2210/04; A61M 2207/00; A61M 37/00; A61M 37/0069; A61B 17/205; A61D 7/00; A61K 9/0021
See application file for complete search history.

(56) References Cited

U.S. PATENT DOCUMENTS

| | | | |
|---|---|---|---|
| 4,702,799 A | 10/1987 | Tuot | |
| 5,017,007 A | 5/1991 | Milne et al. | |
| 5,201,992 A | 4/1993 | Marcus et al. | |
| 5,353,792 A | 10/1994 | Lübbers et al. | |
| 5,449,064 A | 9/1995 | Hogan et al. | |
| 5,457,041 A | 10/1995 | Ginaven et al. | |
| 5,461,482 A | 10/1995 | Wilson et al. | |
| 5,499,474 A | 3/1996 | Knooihuizen | |
| 5,527,288 A | 6/1996 | Gross et al. | |
| 5,611,806 A | 3/1997 | Jang | |
| 5,657,138 A | 8/1997 | Lewis et al. | |
| 5,859,937 A | 1/1999 | Nomura | |
| 5,870,806 A | 2/1999 | Black, Jr. | |
| 5,922,356 A | 7/1999 | Koseki et al. | |
| 5,928,207 A | 7/1999 | Pisano et al. | |
| 5,943,075 A | 8/1999 | Lee et al. | |
| 6,052,652 A | 4/2000 | Lee | |
| 6,233,797 B1 | 5/2001 | Neely et al. | |
| 6,287,556 B1 | 9/2001 | Portnoy et al. | |
| 6,299,621 B1 | 10/2001 | Fogarty et al. | |
| 6,334,856 B1 | 1/2002 | Allen et al. | |
| 6,352,697 B1 | 3/2002 | Cox et al. | |
| 6,454,755 B1 | 9/2002 | Godshall | |
| 6,463,312 B1 | 10/2002 | Bergveld et al. | |
| 6,478,738 B1 | 11/2002 | Hirabayashi et al. | |
| 6,503,231 B1 | 1/2003 | Prausnitz et al. | |
| 6,533,949 B1 | 3/2003 | Yeshurun et al. | |
| 6,537,242 B1 | 3/2003 | Palmer | |
| 6,537,264 B1 | 3/2003 | Cormier et al. | |
| 6,551,849 B1 | 4/2003 | Kenney | |
| 6,557,849 B2 | 5/2003 | Wyss | |
| 6,558,361 B1 | 5/2003 | Yeshurun | |
| 6,565,532 B1 | 5/2003 | Yuzhakov et al. | |
| 6,589,202 B1 | 7/2003 | Powell | |
| 6,591,124 B2 | 7/2003 | Sherman et al. | |
| 6,610,382 B1 | 8/2003 | Kobe et al. | |
| 6,743,211 B1 | 6/2004 | Prausnitz et al. | |
| 6,749,575 B2 | 6/2004 | Matriano et al. | |
| 6,855,372 B2 | 2/2005 | Trautman et al. | |
| 6,881,203 B2 | 4/2005 | Delmore et al. | |
| 6,908,453 B2 | 6/2005 | Fleming et al. | |
| 6,923,764 B2 | 8/2005 | Aceti et al. | |
| 6,931,277 B1 | 8/2005 | Yuzhakov et al. | |
| 6,945,952 B2 | 9/2005 | Kwon | |
| 7,022,071 B2 | 4/2006 | Schaupp et al. | |
| 7,045,069 B2 | 5/2006 | Ozeryansky | |
| 7,048,723 B1 | 5/2006 | Frazier et al. | |
| 7,097,631 B2 | 8/2006 | Trautman et al. | |
| 7,169,600 B2 | 1/2007 | Hoss et al. | |
| 7,211,062 B2 | 5/2007 | Kwon | |
| 7,250,037 B2 | 7/2007 | Shermer et al. | |
| 7,316,665 B2 | 1/2008 | Laurent et al. | |
| 7,753,888 B2 | 7/2010 | Mukerjee et al. | |
| 8,052,633 B2 | 11/2011 | Kendall | |
| 8,062,573 B2 | 11/2011 | Kwon | |
| 8,267,889 B2 | 9/2012 | Cantor et al. | |
| 8,414,548 B2 | 4/2013 | Yuzhakov | |
| 8,540,672 B2 | 9/2013 | McAllister | |
| 8,734,697 B2 | 5/2014 | Chen et al. | |
| 8,883,015 B2 | 11/2014 | Kendall et al. | |
| 9,283,365 B2 | 3/2016 | Kendall et al. | |
| 10,639,823 B2 | 5/2020 | Yamada et al. | |
| 11,464,957 B2 | 10/2022 | Lemaire | |
| 2002/0008530 A1 | 1/2002 | Kim et al. | |
| 2002/0016562 A1 | 2/2002 | Cormier et al. | |
| 2002/0032415 A1 | 3/2002 | Trautman et al. | |
| 2002/0128599 A1 | 9/2002 | Cormier et al. | |
| 2002/0133129 A1 | 9/2002 | Arias et al. | |
| 2002/0169411 A1 | 11/2002 | Sherman et al. | |
| 2002/0177839 A1 | 11/2002 | Cormier et al. | |
| 2003/0036710 A1 | 2/2003 | Matriano et al. | |
| 2003/0090558 A1 | 5/2003 | Coyle et al. | |
| 2003/0199810 A1 | 10/2003 | Trautman et al. | |
| 2003/0199811 A1 | 10/2003 | Sage, Jr. et al. | |
| 2003/0202050 A1 | 10/2003 | Mrvos et al. | |
| 2003/0220656 A1 | 11/2003 | Gartstein et al. | |
| 2004/0002121 A1 | 1/2004 | Regan et al. | |
| 2004/0004649 A1 | 1/2004 | Bibl et al. | |
| 2004/0008241 A1 | 1/2004 | Junhua | |
| 2004/0039397 A1 | 2/2004 | Weber et al. | |
| 2004/0049150 A1 | 3/2004 | Dalton et al. | |
| 2004/0087992 A1 | 5/2004 | Gartstein et al. | |
| 2004/0096455 A1 | 5/2004 | Maa et al. | |
| 2004/0161470 A1 | 8/2004 | Andrianov et al. | |
| 2005/0042866 A1 | 2/2005 | Klapproth et al. | |
| 2005/0089553 A1 | 4/2005 | Cormier et al. | |
| 2005/0089554 A1 | 4/2005 | Cormier et al. | |
| 2005/0126710 A1 | 6/2005 | Laermer et al. | |
| 2005/0137531 A1 | 6/2005 | Prausnitz et al. | |
| 2005/0143713 A1 | 6/2005 | Delmore et al. | |
| 2005/0172956 A1 | 8/2005 | Childers | |
| 2005/0197308 A1 | 9/2005 | Dalton et al. | |
| 2005/0261631 A1* | 11/2005 | Clarke ................ A61K 9/7023 606/186 |
| 2005/0261632 A1 | 11/2005 | Xu | |
| 2006/0012780 A1 | 1/2006 | Nishiyama et al. | |
| 2006/0015061 A1 | 1/2006 | Kuo et al. | |
| 2006/0055724 A1 | 3/2006 | Krawczyk et al. | |
| 2006/0074376 A1 | 4/2006 | Kwon | |
| 2006/0092239 A1 | 5/2006 | Sung et al. | |
| 2006/0195125 A1 | 8/2006 | Sakakine et al. | |
| 2006/0202385 A1 | 9/2006 | Xu et al. | |
| 2006/0264782 A1 | 11/2006 | Holmes et al. | |
| 2007/0027474 A1 | 2/2007 | Lasner | |
| 2007/0060867 A1 | 3/2007 | Xu | |
| 2007/0078376 A1 | 4/2007 | Smith | |
| 2007/0224252 A1 | 9/2007 | Trautman et al. | |
| 2007/0264749 A1 | 11/2007 | Birkmeyer | |
| 2007/0270738 A1 | 11/2007 | Wu et al. | |
| 2007/0293815 A1 | 12/2007 | Chan et al. | |
| 2007/0299388 A1 | 12/2007 | Chan et al. | |
| 2008/0009811 A1 | 1/2008 | Cantor | |
| 2008/0108959 A1 | 5/2008 | Jung et al. | |
| 2008/0114298 A1* | 5/2008 | Cantor ............. A61M 37/0015 604/117 |
| 2008/0136874 A1 | 6/2008 | Tsukamura | |
| 2008/0183144 A1 | 7/2008 | Trautman et al. | |
| 2008/0245764 A1 | 10/2008 | Pirk et al. | |
| 2008/0287858 A1 | 11/2008 | Duan | |
| 2008/0312610 A1 | 12/2008 | Binks et al. | |
| 2008/0312669 A1 | 12/2008 | Vries et al. | |
| 2009/0017210 A1 | 1/2009 | Andrianov et al. | |
| 2009/0041810 A1 | 2/2009 | Andrianov et al. | |
| 2009/0053402 A1 | 2/2009 | Sekiguchi et al. | |
| 2009/0198189 A1 | 8/2009 | Simons et al. | |
| 2009/0292254 A1 | 11/2009 | Tomono | |
| 2010/0121307 A1 | 5/2010 | Lockard et al. | |
| 2010/0221314 A1 | 9/2010 | Matsudo et al. | |
| 2010/0222743 A1 | 9/2010 | Frederickson et al. | |
| 2010/0256568 A1 | 10/2010 | Frederickson et al. | |
| 2010/0271305 A1 | 10/2010 | Chen et al. | |
| 2010/0302322 A1 | 12/2010 | Wang | |
| 2011/0021996 A1 | 1/2011 | Lee et al. | |
| 2011/0028905 A1 | 2/2011 | Takada | |

(56) References Cited

U.S. PATENT DOCUMENTS

| | | | |
|---|---|---|---|
| 2011/0059150 A1 | 3/2011 | Kendall et al. |
| 2011/0160069 A1 | 6/2011 | Corrie et al. |
| 2011/0223542 A1 | 9/2011 | Kendall |
| 2011/0245776 A1 | 10/2011 | Kendall |
| 2011/0276027 A1 | 11/2011 | Trautman et al. |
| 2011/0288484 A1 | 11/2011 | Kendall et al. |
| 2012/0004626 A1 | 1/2012 | Kuwahara et al. |
| 2012/0027810 A1 | 2/2012 | Chen et al. |
| 2012/0041412 A1 | 2/2012 | Roth et al. |
| 2012/0083741 A1 | 4/2012 | Kendall |
| 2012/0083762 A1 | 4/2012 | Kendall |
| 2012/0109065 A1 | 5/2012 | Backes |
| 2012/0136312 A1 | 5/2012 | Terahara et al. |
| 2012/0220981 A1 | 8/2012 | Soo et al. |
| 2012/0265141 A1 | 10/2012 | Kalpin et al. |
| 2012/0277629 A1 | 11/2012 | Bernstein et al. |
| 2012/0330250 A1 | 12/2012 | Kuwahara et al. |
| 2013/0063529 A1 | 3/2013 | Hong et al. |
| 2013/0079666 A1 | 3/2013 | Gonzalez-Zugasti et al. |
| 2013/0106964 A1 | 5/2013 | Rueby et al. |
| 2013/0131598 A1 | 5/2013 | Trautman et al. |
| 2013/0150822 A1 | 6/2013 | Ross |
| 2013/0158468 A1* | 6/2013 | Bernstein ............. A61M 1/38 |
| | | | 604/173 |
| 2013/0158482 A1 | 6/2013 | Davis et al. |
| 2013/0190794 A1 | 7/2013 | Kendall et al. |
| 2013/0296790 A1 | 11/2013 | Masaoka et al. |
| 2013/0337150 A1 | 12/2013 | Biemans |
| 2014/0066842 A1 | 3/2014 | Zhang et al. |
| 2014/0066843 A1 | 3/2014 | Zhang et al. |
| 2014/0117239 A1 | 5/2014 | Sakai et al. |
| 2014/0243747 A1 | 8/2014 | Tokumoto et al. |
| 2014/0257188 A1 | 9/2014 | Kendall et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2015/0057604 A1* | 2/2015 | Arami ............. A61M 37/0015 |
| | | | 29/428 |
| 2015/0080844 A1* | 3/2015 | Donovan ........ A61M 5/14244 |
| | | | 514/12.4 |
| 2015/0097897 A1 | 4/2015 | Redding et al. |
| 2015/0165784 A1 | 6/2015 | Tanaka et al. |
| 2016/0015952 A1 | 1/2016 | Omachi et al. |
| 2016/0058697 A1 | 3/2016 | Kendall et al. |
| 2016/0220483 A1 | 8/2016 | Mistilis et al. |
| 2016/0220803 A1 | 8/2016 | Kendall et al. |
| 2016/0271381 A1 | 9/2016 | Falo, Jr. et al. |
| 2016/0310412 A1 | 10/2016 | Tanoue et al. |
| 2017/0014336 A1 | 1/2017 | Kuruma et al. |
| 2017/0056637 A1 | 3/2017 | Unger et al. |
| 2017/0057124 A1* | 3/2017 | Wakamatsu ......... B29C 39/025 |
| 2017/0065804 A1 | 3/2017 | Uemura |
| 2017/0182301 A1 | 6/2017 | Kendall |
| 2017/0189660 A1 | 7/2017 | Baek |
| 2017/0239458 A1 | 8/2017 | Kato et al. |
| 2017/0282417 A1 | 10/2017 | Okano et al. |
| 2017/0296465 A1 | 10/2017 | Yoshida et al. |
| 2017/0361082 A1 | 12/2017 | Okano et al. |
| 2017/0368322 A1 | 12/2017 | Kato et al. |
| 2018/0008703 A1 | 1/2018 | Johnson |
| 2018/0015271 A1 | 1/2018 | Junger et al. |
| 2018/0058903 A1 | 3/2018 | Hu et al. |
| 2018/0161050 A1 | 6/2018 | Kendall |
| 2018/0263641 A1 | 9/2018 | Crichton et al. |
| 2018/0326726 A1 | 11/2018 | Wang et al. |
| 2019/0001109 A1 | 1/2019 | Kim et al. |
| 2019/0046479 A1 | 2/2019 | Pathak |
| 2019/0049376 A1 | 2/2019 | Widmann et al. |
| 2020/0246545 A1 | 8/2020 | Langer et al. |

FOREIGN PATENT DOCUMENTS

| | | |
|---|---|---|
| CA | 3048102 A1 | 6/2018 |
| CN | 1149018 A | 5/1997 |
| CN | 101214395 A | 7/2008 |
| CN | 101297989 A | 11/2008 |
| CN | 103429222 A | 12/2013 |
| CN | 103718022 A | 4/2014 |
| CN | 104027324 A | 9/2014 |
| CN | 104706626 A | 6/2015 |
| CN | 107206066 A | 9/2017 |
| DE | 102016200271 A1 | 7/2017 |
| EP | 0 139 286 B1 | 8/1991 |
| EP | 0 732 208 A1 | 9/1996 |
| EP | 1 695 734 B1 | 6/2008 |
| EP | 2211089 A1 | 7/2010 |
| EP | 2 213 284 A1 | 8/2010 |
| EP | 2 327 419 A1 | 6/2011 |
| EP | 2 568 174 A1 | 3/2013 |
| EP | 2 835 147 A1 | 2/2015 |
| EP | 3185179 A1 | 6/2017 |
| JP | 2003-127430 A | 5/2003 |
| JP | 2006516205 A | 6/2006 |
| JP | 2007-260889 A | 10/2007 |
| JP | 2008114561 A | 5/2008 |
| JP | 2009276382 A | 11/2009 |
| JP | 2010-071845 A | 4/2010 |
| JP | 2010131123 A | 6/2010 |
| JP | 2013043034 A | 3/2013 |
| JP | 2014111976 A | 6/2014 |
| JP | 2015109963 A | 6/2015 |
| JP | 2016-166769 A | 9/2016 |
| JP | 2016168321 A | 9/2016 |
| JP | 2016535065 A | 11/2016 |
| JP | 2018119810 A | 8/2018 |
| JP | 2022116183 A | 8/2022 |
| WO | 91/06571 A1 | 5/1991 |
| WO | 94/24281 A1 | 10/1994 |
| WO | 98/28037 A1 | 7/1998 |
| WO | 98/28038 A1 | 7/1998 |
| WO | 99/02694 A1 | 1/1999 |
| WO | 99/42564 A2 | 8/1999 |
| WO | 99/64580 A1 | 12/1999 |
| WO | 00/05339 A1 | 2/2000 |
| WO | 00/42215 A1 | 7/2000 |
| WO | WO 0044438 A1 | 8/2000 |
| WO | 00/74763 A2 | 12/2000 |
| WO | 00/74764 A1 | 12/2000 |
| WO | 01/03361 A1 | 1/2001 |
| WO | 01/33614 A1 | 5/2001 |
| WO | 01/85207 A2 | 11/2001 |
| WO | 02/064193 A2 | 8/2002 |
| WO | 02/074173 A1 | 9/2002 |
| WO | 02/075794 A2 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 3/2003 |
| WO | 03/026732 A2 | 4/2003 |
| WO | 03/048031 A2 | 6/2003 |
| WO | 03/053258 A1 | 7/2003 |
| WO | 03/092785 A1 | 11/2003 |
| WO | 2004/000389 A2 | 12/2003 |
| WO | 2004/024224 A1 | 3/2004 |
| WO | WO 2005018703 A2 | 3/2005 |
| WO | 2005/049108 A2 | 6/2005 |
| WO | 2005/060621 A2 | 7/2005 |
| WO | 2005/069736 A2 | 8/2005 |
| WO | 2005/072360 A2 | 8/2005 |
| WO | 2005/072630 A1 | 8/2005 |
| WO | 2005/123173 A1 | 12/2005 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A2 | 12/2006 |
| WO | 2007/002123 A2 | 1/2007 |
| WO | 2007/002521 A2 | 1/2007 |
| WO | 2007/012114 A1 | 2/2007 |
| WO | 2007/030477 A2 | 3/2007 |
| WO | 2007/054090 A1 | 5/2007 |
| WO | 2007/061781 A1 | 5/2007 |
| WO | 2007/061871 A1 | 5/2007 |

(56) References Cited

FOREIGN PATENT DOCUMENTS

| WO | 2007/070004 A2 | 6/2007 |
|---|---|---|
| WO | WO 2007064486 A1 | 6/2007 |
| WO | 2007/080427 A2 | 7/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2008/083209 A2 | 7/2008 |
| WO | 2008/091602 A2 | 7/2008 |
| WO | 2009/040548 A1 | 4/2009 |
| WO | 2009/066763 A1 | 5/2009 |
| WO | WO 2009077859 A1 | 6/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | WO 2010001671 A1 | 1/2010 |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |
| WO | 2012/119907 A1 | 9/2012 |
| WO | 2012/122162 A1 | 9/2012 |
| WO | 2013/053022 A1 | 4/2013 |
| WO | 2013/055641 A1 | 4/2013 |
| WO | WO 2013110124 A1 | 8/2013 |
| WO | 2014/058746 A1 | 4/2014 |
| WO | WO 2015022833 A1 | 2/2015 |
| WO | 2015/034924 A1 | 3/2015 |
| WO | WO 2016090356 A1 | 6/2016 |
| WO | WO 2016098780 A1 | 6/2016 |
| WO | 2016/123665 A1 | 8/2016 |
| WO | 2016/143514 A1 | 9/2016 |
| WO | 2017/123652 A1 | 7/2017 |
| WO | 2018/119174 A1 | 6/2018 |
| WO | WO 2019213218 A1 | 11/2019 |

OTHER PUBLICATIONS

Albert et al., "Dendritic cells acquire antigen from apoptotic cells and induce class I-restricted CTLs," *Nature* 392:86-89, 1998.
Albert et al., "Tumor-specific killer cells in paraneoplastic cerebellar degeneration," *Nature Medicine* 4(11):1321-1324, 1998.
Anderson, "Cutaneous Microdialysis: Is it Worth the Sweat?," *Journal of Investigative Dermatology* 126:1207-1209, 2006.
Athanasopoulos et al., "Gene therapy vectors based on adeno-associated Virus: Characteristics and applications to acquired and inherited diseases (Review)," *International Journal of Molecular Medicine* 6:363-375, 2000.
Australian Examination Report No. 1 dated Oct. 9, 2020 for Australian Application No. 2016333148, 5 pages.
Australian Examination report No. 2 for standard patent application, dated Jan. 9, 2017, for Australian Application No. 2012323782, 4 pages.
Australian Patent Examination Report No. 1, dated Apr. 11, 2016, for Australian Application No. 2012323782, 3 pages.
Australian Patent Examination Report No. 1, issued Mar. 27, 2013, for Australian Application No. 2009212106, 5 pages.
Bachmann et al., "Dendritic cells process exogenous viral proteins and virus-like particles for class I presentation to CD8[+] cytotoxic T lymphocytes," *Eur. J. Immunol.* 26:2595-2600, 1996.
Boehm et al., "Inkjet printing for pharmaceutical applications," *Materials Today* 17(5):247-252, 2014.
Camilli et al., "*Listeria monocytogenes* Mutants Lacking Phosphatidylinositol-specific Phospholipase C Are AVirulent," *J. Exp. Med.* 173:751-754, 1991.
Canadian Office Action, dated Apr. 23, 2015, for Canadian Application No. 2,749,347, 4 pages.
Canadian Offce Action, dated Feb. 17, 2015, for Canadian Application No. 2,745,339, 4 pages.

Chinese 1st Office Action, issued Feb. 17, 2012, for Chinese Application No. 200980104635.3, 13 pages. (with English Translation).
Chinese 2nd Office Action, dated Sep. 24, 2012, for Chinese Application No. 200980104635.3, 9 pages. (with English Translation).
Chinese 3rd Office Action, dated Dec. 28, 2012, for Chinese Application No. 200980104635.3, 6 pages. (with English Translation).
Chinese Office Action dated Jan. 11, 2021 for Chinese Application No. 201880036675.8, 31 pages. (w/ machine translation).
Communication pursuant to Article 94(3) EPC, dated Jan. 19, 2021, for European Application No. 16 746 000.5, 4 pages.
Cormier et al., "Transdermal delivery of desmopressin using a coated microneedle array patch 3 stem," *Journal of Controlled Release* 97:503-511, 2004.
Cox et al., "Adjuvants—a classification and review of their modes of action," *Vaccine* 15(3):248-256, 1997.
Crichton et al., "The effect of strain rate on the precision of penetration of short densely-packed microprojection array patches coated with vaccine," *Biomaterials* 31(16):4562-4572, 2010.
Crichton et al., "The viscoelastic, hyperelastic and scale dependent behaviour of freshly excised individual skin layers," *Biomaterials* 32:4670-4681, 2011.
Desai et al., "Understanding release kinetics of biopolymer drug delivery microcapsules for biomedical applications," *Materials Science and Enf(ineerinf( BI* 68:127-131, 2010.
Dreyer, "Microneedles: Microprocessing in Medicine," Final Presentation ENMA465 Project, May 10, 2004, URL=http://www.mse.umd.edu/undergrad/courses/ENMA465-project-results.html, 23 pages.
European Search Report mailed Sep. 10, 2018, for European Application No. 16746000.5, 3 pages.
Extended European Search Report dated Feb. 15, 2021 for European Application No. 18816698.7-1230, 8 pages.
Extended European Search Report, dated Jul. 20, 2012, for European Application No. 09833918.7-1526, 9 pages.
Extended European Search Report, dated Nov. 10, 2015, for European Application No. 12840561.0-1506, 11 pages.
Extended European Search Report dated Nov. 30, 2020 for European Application No. 18776793.4-1010, 10 pages.
Extended European Search Report, dated Sep. 26, 2014, for European Application No. 09707729.1-1508, 9 pages.
Feng et al., "Molecular Biomarkers For Cancer Detection in Blood and Bodily Fluids," *Critical Reviews in Clinical Laboratory Sciences* 43(5-6):497-560, 2006.
Fernando et al., "Potent Immunity to Low Doses ofInfluenza Vaccine by Probabilistic Guided Micro-Targeted Skin Delivery in a Mouse Model," *PLoS One* 5(4):e10266, 2010. (11 pages).
Fernando et al., "Safety, tolerability, acceptability and immunogenicity of an influenza vaccine delivered to human skin by a novel high-density microprojection array patch (Nanopatch™)," *Vaccine* 36:3779-3788, 2018.
Fernando et al., "Influenza nucleoprotein DNA vaccination by a skin targeted, dry coated, densely packed microprojection array (Nanopatch) induces potent antibody and CD8+ T cell responses," *Journal of Controlled Release* 237:35-41, 2016.
Gao et al., "Priming of Influenza Virus-Specific Cytotoxic T Lymphocytes Vivo By Short Synthetic Peptides," *The Journal of Immunology* 147(10):3268-3273, 1991.
Garafalo et al., "Histamine release and therapy of severe dermatographism," *The Journal of Allergy and Clinical Immunology* 68(2):103-105, 1981.
Gardeniers et al., "Silicon Micromachined Hollow Microneedles for Transdermal Liquid Transport," *Journal of Microelectromechanical Systems* 12(6):855-862, 2003.
Gill et al., "Coated microneedles for transdermal delivery," *Journal of Controlled Release* 117(2):227-237, 2007.
Gill et al., "Coating Formulations for Microneedles," *Pharmaceutical Research* 24(7):1369-1380, 2007.
Henry et al., "Microfabricated Microneedles: A Novel Approach to Transdermal Drug Delivery," *Journal of Pharmaceutical Sciences* 87(8):922-925, 1998.
International Preliminary Report on Patentability dated Feb. 4, 2020 for International Application No. PCT/AU2018/050810, 9 pages.

(56) References Cited

OTHER PUBLICATIONS

International Preliminary Report on Patentability, dated Jun. 7, 2006, for International Application No. PCT/GB2005/000336, 9 pages.
International Preliminary Report on Patentability, dated Jun. 29, 2010, for International Application No. PCT/AU2008/001903, 7 pages.
International Preliminary Report on Patentability, dated Nov. 14, 2012, for International Application No. PCT/AU2011/000890, 6 pages.
International Search Report and Written Opinion, mailed Dec. 6, 2016, for International Application No. PCT/AU2016/050867, 20 pages.
International Search Report and Written Opinion, mailed Dec. 22, 2016, for International Application No. PCT/AU2016/050907, 14 pages.
International Search Report and Written Opinion, mailed Feb. 20, 2009, for International Application No. PCT/AU2008/001903, 11 pages.
International Search Report and Written Opinion, mailed Mar. 7, 2016, for International Application No. PCT/AU2016/050056, 13 pages.
International Search Report, mailed Feb. 20, 2013, for International Application No. PCT/AU2012/001289, 13 pages.
International Search Report mailed Aug. 1, 2018, for International Application No. PCT/AU2018/050586, 4 pages.
International Search Report dated Jul. 30, 2018, for International Application No. PCT/AU2018/050298, 6 pages.
International Search Report, mailed Oct. 25, 2011, for International Application No. PCT/AU2011/000890, 4 pages.
International Search Report mailed May 25, 2020 for International Application No. PCT/AU2020/050296, 6 pages.
International Search Report mailed Nov. 8, 2018, for International Application No. PCT/AU2018/050810, 8 pages.
International Search Report dated Sep. 13, 2018, for International Application No. PCT/AU2018/050847, 4 pages.
Ito et al., "Evaluation of self-dissolving needles containing low molecular weight heparin (LMWH) in rats," *International Journal of Pharmaceutics* 349:124-129, 2008.
Ito et al., "Feasibility of microneedles for percutaneous absorption of insulin," *European Journal of Pharmaceutical Sciences* 29:82-88, 2006.
Ito et al., "Self-dissolving microneedles for the percutaneous absorption of EPO in mice," *Journal of Drug Targeting* 14(5):255-261, 2006.
Jondal et al., "MHC Class I-Restricted CTL Responses to Exogenous Antigens," *Immunity* 5:295-302, 1996.
Kay et al., "Viral vectors for gene therapy: the art of turning infectious agents into vehicles of therapeutics," *Nature Medicine* 7(1):33-40, 2001.
Kendall et al., "The mechanical properties of the skin epidermis in relation to targeted gene and drug delivery," *Biomaterials* 28:4968-4977, 2007.
Kuzu et al., "In vivo priming effect during various stages of ontogeny of an influenza A virus nucleoprotein peptide," *Eur. J. Immunol.* 23:1397-1400, 1993.
Kwon et al., "In Vitro Modeling of Transdermal PTH Delivery by Dissolving Micro-needle Patch," *34th Annual Meeting & Exposition of the Controlled Release Society*, Long Beach, California, USA, Jun. 5, 2007, 2 pages.
Kwon et al., "Rapid Intradermal Drug Delivery by a Dissolvable Micro-Needle Patch," *32nd Annual Meeting & Exposition of the Controlled Release Society*, Miami, Florida, USA, Jun. 18-22, 2005, 2 pages.
Kwon, "Acne Treatment by a Dissolvable Micro-Needle Patch," *33rd Annual Meeting & Exposition of the Controlled Release Society*, Vienna, Austria, Jul. 24, 2006, 2 pages.
Kwon, "In Vitro Evaluation of Transdermal Drug Delivery by a Micro-needle Patch," *31st Annual Meeting & Exposition of the Controlled Release Society*, Honolulu, Hawaii, USA, Jun. 12-16, 2004, 2 pages.
Lee et al., "Dissolving microneedles for transdermal drug delivery," *Biomaterials* 29:2113-2124, 2008.
Lin et al., "Silicon-Processed Microneedles," *IEEE Journal of Microelectromechanical Systems* 8(1):78-84, 1999.
Ma et al., "A PZT Insulin Pump Integrated with a Silicon Micro Needle Array for Transdermal Drug Delivery," *56th Electronic Components & Technology Conference*, San Diego, CA, May 30-Jun. 2, 2006, 5 pages.
Ma et al., "Coating solid dispersions on microneedles via a molten dip coating method: 12 development and in vitro evaluation for transdermal delivery of a water insoluble drug," *J Pharm Sci* 103(11):3621-3630, 2014. (21 pages).
Matriano et al., "Macroflux® Microprojection Array Patch Technology: A New and Efficient Approach for Intracutaneous Immunization," *Pharmaceutical Research* 19(1):63-70, 2002.
McAllister et al., "Microfabricated needles for transdermal delivery of macromolecules and nanoparticles: Fabrication methods and transport studies," *PNAS* 100(24): 13755-13760, 2003.
Meléndez et al., "Thermal Inkjet Application in the Preparation of Oral Dosage Forms: Dispensing of Prednisolone Solutions and Polymorphic Characterization by Solid-State Spectroscopic Techniques," *Journal of Pharmaceutical Sciences* 97(7):2619-2636, 2008.
Mengaud et al., "Expression in *Escherichia coli* and Sequence Analysis of the Listeriolysin O Determinant of *Listeria monocytogenes*," *Infection and Immunity* 56(4):766-772, 1988.
Miyano et al., "Hydrolytic Microneedles as Transdermal Drug Delivery System," *14th International Conference on Solid-State Sensors, Actuators and Microsystems*, Lyon, France, Jun. 10-14, 2007, pp. 355-358.
Miyano et al., "Sugar Micro Needles as Transdermic Drug Delivery System," *Biomedical Microdevices* 7(3):185-188, 2005.
Moore et al., "Introduction of Soluble Protein into the Class I Pathway of Antigen Processing and Presentation," *Cell* 54:777-785, 1988.
Mukerjee et al., "Microneedle array for transdermal biological fluid extraction and in situ analysis," *Sensors and Actuators A* 114:267-275, 2004.
Muller et al., "High-density microprojection array delivery to rat skin of low doses of trivalent inactivated poliovirus vaccine elicits potent neutralising antibody responses," *Scientific Reports* 7:12644, 2017. (10 pages).
Ng et al., "Potent response of QS-21 as a vaccine adjuvant in the skin when delivered with the Nanopatch, resulted in adjuvant dose sparing," *Scientific Reports* 6:29368, 2016. (12 pages).
Oh et al., "Demonstration of Dose-controlled Delivery by Dissolvable Micro-needle Arrays," *34th Annual Meeting & Exposition of the Controlled Release Society*, Long Beach, California, USA, Jun. 5, 2007, 2 pages.
Oh et al., "Intradermal influenza vaccine delivery using skin-penetrating dissolvable vaccine microneedles," *AAPS Annual Meeting and Exposition*, San Antonio, Texas, USA, Oct. 29-Nov. 2, 2006, 1 page.
Palmer et al., "Streptolysin O: A Proposed Model of Allosteric Interaction between a Pore-Forming Protein and Its Target Lipid Bilayer," *Biochemistry* 37:2378-2383, 1998.
Park et al., "Biodegradable polymer microneedles: Fabrication, mechanics and transdermal drug delivery," *Journal of Controlled Release* 104:51-66, 2005.
Park et al., "Polymer Microneedles for Controlled-Release Drug Delivery," *Pharmaceutical Research* 23(5):1008-1019, 2006.
Park et al., "Towards the silicon nanowire-based sensor for intracellular biochemical detection," *Biosensors and Bioelectronics* 22:2065-2070, 2007.
Portnoy et al., "Capacity of Listeriolysin O, Streptolysin O, and Perfringolysin O To Mediate Growth of *Bacillus subtilis* within Mammalian Cells," *Infection and Immunity* 60(7):2710-2717, 1992.
Radulescu et al., "Uniform Paclitaxel-Loaded Biodegradable Microspheres Manufactured by Ink-Jet Technology," *Proc., the*

(56) References Cited

OTHER PUBLICATIONS

*Winter Symposium and I Ith International Symposium on Recent Advantages in Drug-Delivery Systems, Controlled Release Society,* Salt Lake City, Utah, 2003, 5 pages.

Rossjohn et al., "Structure of a Cholesterol-Binding, Thiol-Activated Cytolysin and a Model of Its Membrane Form," *Cell* 89:685-692, 1997.

Sandler et al., "Inkjet Printing of Drug Substances and Use of Porous Substrates-Towards Individualized Dosing," Journal of Pharmaceutical Sciences 100(8):3386-3395, 2011.

Schulz et al., "Peptide-induced antiviral protection by cytotoxic T cells," *Proc. Natl. Acad. Sci. USA* 88:991-993, 1991.

Scoutaris et al., "Current Trends on Medical and Pharmaceutical Applications of Inkjet Printing Technology," *Pharm Res.* 33:1799-1816, 2016.

Scoutaris et al., "ToF-SIMS analysis of chemical heterogenities in inkjet micro-array printed drug/polymer formulations," *J Mater Sci: Mater Med* 23:385-391, 2012.

Silver et al., "Viscoelastic Properties of Young and Old Human Dermis: A Proposed Molecular Mechanism for Elastic Energy Storage in Collagen and Elastin," *J. Appl. Polym. Sci.* 86:1978-1985, 2002.

Stoeber et al., "Arrays of Hollow Out-of-Plane Microneedles for Drug Delivery," *Journal of Microelectromechanical Systems* 14(3):472-479, 2005.

Sullivan et al., "Minimally Invasive Protein Delivery with Rapidly Dissolving Polymer Microneedles," *Adv. Mater.* 20:933-938, 2008.

Tao et al., "A systematic study of dry etch process for profile control of silicon tips," *Microelectronic Engineering* 78-79:147-151, 2005.

Tarcha et al., "The Application of Ink-Jet Technology for the Coating and Loading of Drug-Eluting Stents," *Annals of Biomedical Enf(ineerinf(* 35(10): 1791-1799, 2007.

Tsuchiya et al., "Development of Blood Extraction System for Health Monitoring System," *Biomedical Microdevices* 7(4):347-353, 2005.

Tyagi et al., "Molecular Beacons: Probes that Fluoresce upon Hybridization," *Nature Biotechnology* 14:303-308, 1996.

Vigna et al., "Lentiviral vectors: excellent tools for experimental gene transfer and promising candidates for gene therapy," *The Journal of Gene Medicine* 2:308-316, 2000.

Walther et al., "Viral Vectors for Gene Transfer: A Review of Their Use in the Treatment of Human Diseases," *Drugs* 60(2):249-271, 2000.

Wang et al., "Label-free hybridization detection of a single nucleotide mismatch by immobilization of molecular beacons on an agarose film," *Nucleic Acids Research* 30(12):e61, 2002. (9 pages).

Widera et al., "Effect of delivery parameters on immunization to ovalbumin following intracutaneous administration by a coated microneedle array patch system," *Vaccine* 24:1653-1664, 2006.

Wu et al., "Production of viral vectors for gene therapy applications," *Current Opinions in Biotechnology* 11:205-208, 2000.

Wu et al., "Solid free-form fabrication of drug delivery devices," *Journal of Controlled Release* 40:77-87, 1996.

Yuan et al., "Measuring microelastic properties of stratum corneum," *Colloids and Surfaces B: Biointerfaces* 48:6-12, 2006.

Zheng et al., "Multiplexed electrical detection of cancer markers with nanowire sensor arrays," *Nature Biotechnology* 23(10):1294-1301, 2005.

Zhou et al., "Liposome-Mediated Cytoplasmic Delivery of Proteins: An Effective Means of Accessing the MHC Class I-Restricted Antigen Presentation Pathway," *Immunomethods* 4:229-235, 1994.

Fernando et al., "Safety, tolerability, acceptability and immunogenicity of an influenza vaccine delivered to human skin by a novel high-density microprojection array patch (Nanopatch™M)," *Vaccine* 36:3779-3788, 2018.

U.S. Appl. No. 14/351,499, filed Apr. 11, 2014, Delivery Device.
U.S. Appl. No. 17/089,446, filed Nov. 4, 2020, Delivery Device.
U.S. Appl. No. 15/849,134, filed Dec. 20, 2017, Method of Delivering Material or Stimulus to a Biological Subject.
U.S. Appl. No. 16/896,387, filed Jun. 9, 2020, Delivery Device.
U.S. Appl. No. 15/548,065, filed Aug. 1, 2017, Microprojection Array Applicator and Method.
U.S. Appl. No. 15/760,869, filed Mar. 16, 2018, Microprojection Arrays With Microprojections Having Large Surface Area Profiles.
U.S. Appl. No. 15/942,895, filed Apr. 2, 2018, Device and Method for Coating Surfaces.
U.S. Appl. No. 16/622,092, filed Dec. 12, 2019, Quality Control of Substrate Coatings.
U.S. Appl. No. 16/636,467, filed Feb. 4, 2020, Compact High Mechanical Energy Storage and Low Trigger Force Actuator for the Delivery of Microprojection Array Patches (MAP).
U.S. Appl. No. 16/638,072, filed Feb. 10, 2020, Differential Coating of Microprojections and Microneedles on Arrays.
Chinese Office Action dated Feb. 14, 2022 for Chinese Application No. 1 201880036675.8, 12 pages.
Japanese Office Action dated Feb. 8, 2022 for Japanese Application No. 2019-2554394, 6 pages.
Extended European Search Report, dated Jan. 1, 2023, for European Application No. 207832809-1122, 9 pages.
Office Action, mailed Jan. 17, 2023, for U.S. Appl. No. 17/241,927, Meliga et al., "Microprojection Arrays With Enhanced Skin Penetrating Properties and Methods Thereof," 47 pages.
Canadian Office Action, mailed Jan. 5, 2023, for Canadian Application No. AU2016050907, 5 pages.
European Office Action, dated Dec. 13, 2022, for European Application No. 18844031.7-1111, 3 pages.
Office Action, dated Dec. 20, 2023, for Canadian Patent Application No. 2,999,538. (4 pages).
Office Action, dated Dec. 26, 2023, for Indian Patent Application No. 3047/DELNP/2014. (3 pages).
Office Action, dated Dec. 5, 2023, for Canadian Patent Application No. 3,135,302. (4 pages).
Office Action, dated Nov. 24, 2023, for Canadian Patent Application No. 3,065,371. (9 pages).
Office Action, with English Translation, dated Jan. 20, 2024, for Chinese Patent Application No. 202080040017.3 (10 pages).
Office Action, with English Translation, dated Jan. 9, 2024, for Japanese Patent Application No. 2021-557686. (15 pages).
Examination Report No. 1, dated Aug. 30, 2023, for International Patent Application AU2018309562. (4 pages).
Examination Report, dated Jun. 16, 2023, for International Patent Application EP16849947.3-1002. (5 pages).
International Search Report, dated Jul. 4, 2023, for Application EP22213943.8-1122. (7 pages).
International Search Report, dated Jun. 26, 2023, for Application EP22214247.3-1009. (7 pages).
Masters et al., "Multiphoton Excitation Microscopy and Spectroscopy of Cells, Tissues and Human Skin In Vivo", *Biophysical Journal* 72(6):2405-2412, Jun. 1997.
Masters et al., "Multiphoton Excitation Microscopy and Spectroscopy of Cells, Tissues, and Human Skin In Vivo," Fluorescent and Luminescent Probes for Biological ActivitV, 2:414-432, Dec. 1999.
Notice of Allowance, dated Aug. 23, 2023 for U.S. Appl. No. 17/323,671, Junger et al., "Quality Control of Substrate Coatings." 9 pages.
Office Action, dated Jul. 25, 2023, for International Application JP2022-076841. (3 pages).
Office Action, dated Oct. 3, 2023, for Canadian Patent Application 3,072,369. (4 pages).
Office Action, dated Sep. 21, 2023, for International Application 18841863.6-1009. (3 pages).
Extended European Search Report, dated Mar. 12, 2024, for European Patent Application No. 23199211.6. (10 pages).
International Search Report and Written Opinion, dated Mar. 21, 2024, for International Patent Application No. PCT/AU2024/050067. (23 pages).
Office Action, dated Apr. 27, 2024, for Chinese Patent Application No. 202080040017.3. (10 pages).
Office Action, dated Mar. 28, 2024, for Canadian Patent Application No. 3,071,680. (10 pages).

\* cited by examiner

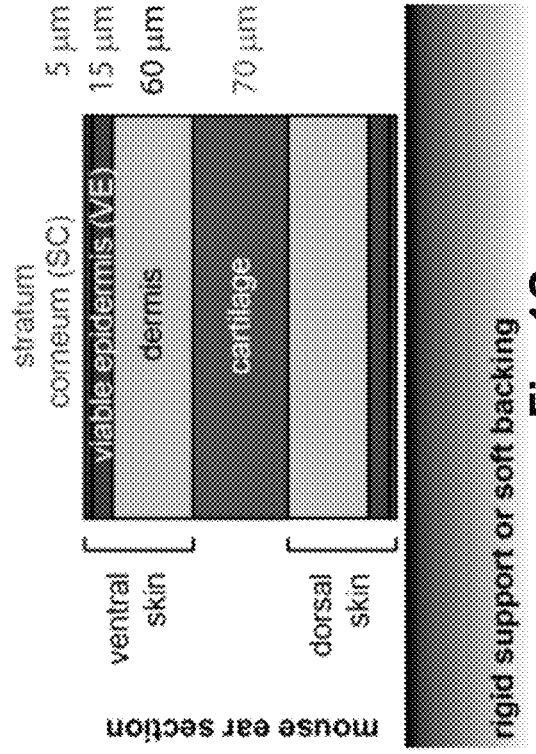
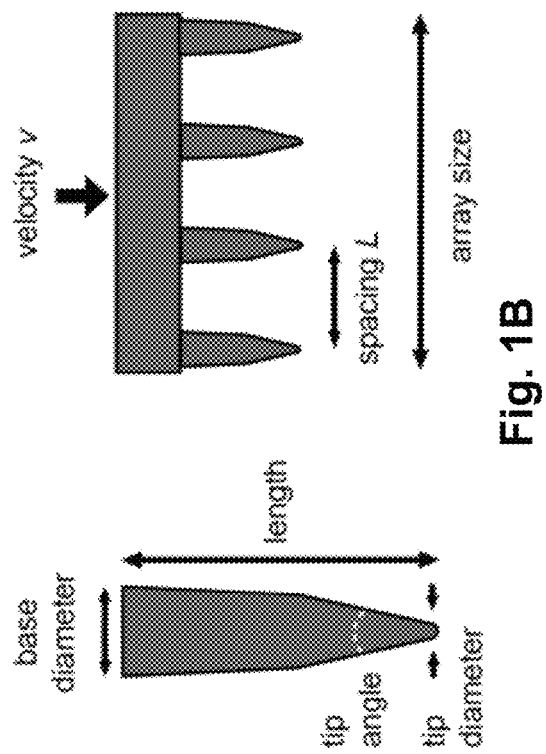
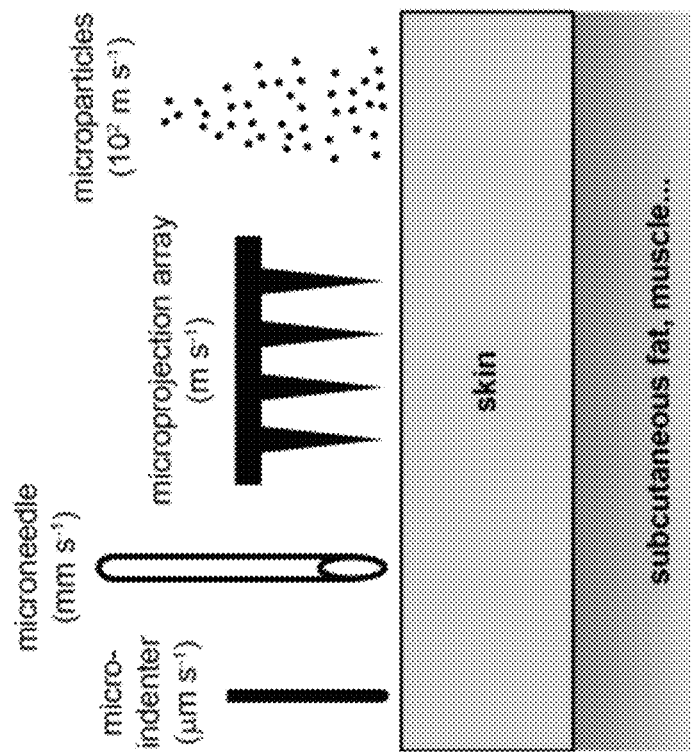
Fig. 1A
Fig. 1B
Fig. 1C

МICROPROJECTION ARRAYS WITH ENHANCED SKIN PENETRATING PROPERTIES AND METHODS THEREOF

BACKGROUND OF THE INVENTION

The invention is generally directed to devices and methods for intradermal delivery of active agents into the skin, more particularly the invention is directed to devices and methods for improving the immunogenicity of vaccine preparations by intradermal delivery of the vaccine via a microprojection array in which the parameters for delivery of the active agents have been developed to achieve appropriate depth penetration and efficient delivery of the active agent.

DESCRIPTION OF THE PRIOR ART

Next-generation healthcare increasingly relies on minimally-invasive biomedical devices capable of negotiating skin mechanical properties to mediate intracutaneous and transcutaneous tasks like administering therapeutics, extracting diagnostic biomarkers and performing surgical procedures. For instance, epidermal and dermal targeted delivery of vaccines is a promising candidate for increasing global vaccine coverage, due to ease of access as well as unique immunological properties of the skin. Passive permeation of the antigen is impractical due to the large molecular size of most antigens, therefore, the payload is actively transported to the viable-cell strata by mechanically breaching through the skin's outer barriers. This transport is typically achieved by either: 1) high-pressure jet injectors that fire the payload in liquid or powder form (microparticles) or 2) penetrator tips that deposit payload through a channel in the skin (e.g. intradermal syringe needles and hollow microneedles), or that embed the payload in a matrix/coating that dissolves in the skin (e.g. dissolvable/coated microneedle and microprojection arrays). Some studies have reported improved immune responses compared to standard syringe injection. In addition, the mechanisms underlying the low-dose efficacy or increased potency are not yet fully understood thereby limiting the potential of cutaneous vaccination.

Precise penetration to the targeted depth for vaccine uptake by site-specific cells is of fundamental importance and relies on negotiating the unique elastic and failure properties of the skin which is a multilayer composite 'material'. Despite the many published mechanical characterization and underlying linear and non-linear elastic models, there is a paucity of investigations focusing on skin elastic and failure behavior in mechanical conditions relevant for epidermal and dermal delivery of active agents including vaccines. There are reasons beyond the skin's intrinsic structural complexity, and inter-species (e.g. mouse vs human), inter-individual (ethnicity, gender) and intra-individual (age, body site) variabilities for this failure. Firstly, the persistent assumption of skin homogeneity and isotropicity resulted in different elastic moduli depending on the loading mode. Secondly, the Young's moduli extrapolated from indentations showed a marked inverse dependence with the probe diameter. Thirdly, although the extensive literature on skin viscoelasticity provides solid evidence of the rate-dependence of skin elasticity, there appear to be no published out-of-plane tests where the load was applied at velocities >1 m s$^{-1}$ or strain rates >1 μs$^{-1}$.

While underlying linear-elastic and hyperelastic descriptions are corroborated by empirical data, skin also lacks established constitutive models of failure. Skin penetration by individual needles has typically been described using either: 1) stress-based failure criteria extend the traditional yield criteria such that the skin fails when the stress (typically the von Mises component) exceeds a threshold strength; as such, this framework does not account for the irrecoverable energy dissipated into material damage and, thus, for example, cannot be used to predict the depth achieved by penetrators fired at a given velocity; or 2) energy-based fracture propagation extends the concept of fracture toughness to ductile materials, i.e. an energy per unit area representing the cost to create crack interfaces. This model, though, does not specify if an initial notch forms at all (failure initiation), how the crack propagates (e.g. direction and speed), and what fraction of the penetrator energy is utilized in the fracture (as opposed of being elastically stored or dissipated in viscous or plastic phenomena). Rather, the prediction of skin penetration requires a complete description of the spatial stress-strain distributions to detect the instant and coordinates of failure initiation, and the energy repartition among various reversible and irreversible phenomena.

Skin out-of-plane mechanical properties of skin at the microscale are typically measured ex vivo using indentation (e.g. AFM) at velocities up to ~100 μm s$^{-1}$; however, vaccines are delivered in vivo across the skin's superficial barriers using penetrators applied (by hand or impact applicators) at velocities >>mm s$^{-1}$; strain-rate effects and subcutaneous layers play an important mechanical role during skin penetration.

The limited understanding of skin elastic response to high strain rates, mechanisms of failure and fracture, and interaction with multiple penetrators have prevented the rational design of epidermal and dermal targeted vaccination devices. Some microprojection arrays are silicon chips containing, on one side, thousands of densely-arranged (>>1,000 cm$^{-2}$) microprojections, i.e. solid cone-like structures measuring ~100 μm in length. Notably, application of vaccine-coated microprojection arrays to mouse skin elicited immune response using ~1/100 of the dose required by intramuscular injection. The precise and consistent targeting of specific strata within the skin is important and achieved by applying the array against the skin at controlled velocities (~1 m s$^{-1}$). Therefore, there is a need for in-depth understanding of the skin mechanical interaction with microneedles/microprojections which would allow the tailoring of an array design and application conditions to achieve customized antigen placement and to increase the targeting consistency across patients and minimize the penetration energy of the array while controlling skin inflammation, tolerability and acceptability.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE PRESENT INVENTION

In a broad form the present invention seeks to provide an apparatus for delivering an active ingredient into the skin of an animal at a defined depth, the apparatus including:
a) a microprojection array including a plurality of microprojections having a density of at least 2,000 projections per cm$^2$; and, b) an applicator that drives the microprojection array towards the skin in use so that the microprojection array impacts on the skin with a mass-to-velocity ratio of between 0.0005 g/m/s and 0.1 g/m/s per cm$^2$.

Typically the microprojection array impacts on the skin with a mass-to-velocity ratio of at least one of:
a) less than 0.05 g/m/s;
b) less than 0.005 g/m/s; and,
c) between 0.033 g/m/s and 0.0008 g/m/s.

Typically the microprojection array impacts the skin with a mass between at least one of:
a) 0.001 g and 5 g;
b) 0.005 g and 2 g; and,
c) 0.02 g and 0.5 g.

Typically the microprojection array impacts the skin at velocities between:
a) 5 m/s and 50 m/s;
b) 10 m/s g and 30 m/s; and,
c) 15 m/s and 25 m/s.

Typically the microprojection array has an area between at least one of:
a) 16 mm$^2$ and 400 mm$^2$;
b) 36 mm$^2$ and 225 mm$^2$; and,
c) 64 mm$^2$ and 100 mm$^2$.

Typically the microprojection array has a microprojection density between 5,000 and 20,000 projections per cm$^2$.

Typically the microprojections are at least one of:
a) solid;
b) non-porous; and,
c) non-hollow.

Typically the microprojections are at least one of:
a) tapered;
b) substantially conical;
c) substantially flattened;
d) hexagonal; and,
e) octagonal.

Typically the microprojections have a length of at least one of:
a) more than 100 µm;
b) more than 200 µm;
c) less than 1000 µm;
d) less than 5000 µm; and,
e) between 200 µm and 300 µm.

Typically the microprojections include:
a) a base having a width of about 5 µm to about 50 µm; and,
b) a tip having a width of about 0.5 µm to about 2 µm.

Typically the applicator includes a driver that drives the microprojection array towards the skin and wherein the microprojection array is releasably mounted to the driver so that the microprojection array is released from the driver prior to the microprojections contacting the skin.

Typically the driver abuts against a stop to thereby release the microprojection array.

Typically the stop includes an annular shoulder.

Typically the applicator includes:
a) a housing containing the driver; and,
b) a substantially tubular spacer that in use is positioned with an open end in contact with a surface of the skin to thereby space the housing from the skin, the stop being provided proximate the open end of the spacer.

Typically the driver is urged from a retracted to an extended position using a biasing mechanism, and wherein the biasing mechanism and engagement between the driver and housing define a driver velocity in use.

Typically the driver is a piston.

Typically the biasing mechanism includes at least one of:
a) a spring; and,
b) a pneumatic actuator.

Typically the engagement is frictional engagement between a piston and piston chamber within the housing.

Typically the microprojection array impacts on the skin with a mass-to-velocity ratio sufficiently high to effect at least one of:
a) fracture the skin;
b) concentrate mechanical stress in superficial layers of the skin;
c) invoke strain-rate dependent skin stiffening;
d) cause consistent penetration independent of variations in subcutaneous properties of the skin;
e) dissipate inertia so as to avoid mechanical stress on body parts underlying the skin; and,
f) cause a controlled amount of mechanical stress for immune-enhancing inflammation.

Typically at least tips of the microprojections are coated.

Typically the active ingredient is one or more vaccine antigens.

In another broad form the present invention seeks to provide a method of determining the design of a microprojection array and the velocity for delivering the microprojection array to a predetermined range of skin depth comprising calculating the microprojection array density, microprojection array area, microprojection array mass and microprojection velocity to mass ratio to deliver the microprojection array to the predetermined depth range.

BRIEF DESCRIPTION OF THE DRAWINGS

An example of the present invention will now be described with reference to the accompanying drawings, in which:—

FIG. 1A is a schematic drawing of various modes of penetrating the skin;

FIG. 1B is a schematic diagram of design specifications for individual and arrays of penetrators (e.g. microneedles/microprojections);

FIG. 1C is a schematic drawing of a mouse ear section and skin layer thickness;

FIG. 2A is a plot of Young's moduli versus the strain rate and velocity for the stratum corneum; FIG. 2B is a plot of Young's moduli versus the strain rate and velocity for the viable epidermis; FIG. 2C is a plot of Young's moduli versus the strain rate and velocity for the dermis; FIG. 2D is a plot of the stretch exponent versus the strain rate and velocity for the stratum corneum;

FIG. 2E is a plot of the stretch exponent versus the strain rate and velocity for the viable epidermis; FIG. 2F is a plot of the stretch exponent versus the strain rate and velocity for the dermis; and FIGS. 2G and 2H are bar diagrams of Young's modulus and stretch exponent extrapolated for a probe measuring 1 µm in diameter indenting the skin layers in the velocity range 0.3-10 m s$^{-1}$ (or strain-rate range 0.3-10 µs$^{-1}$);

FIG. 3A shows VM stress in the skin during the penetration of arrays characterized by projection densities of ~0 proj cm$^{-2}$ (infinitely-spaced projections); FIG. 3B shows VM stress in the skin during the penetration of arrays characterized by projection densities of 5,000 proj cm$^{-2}$; FIG. 3C shows VM stress in the skin during the penetration of arrays characterized by projection densities of 10,000 proj cm$^{-2}$; and FIG. 3D shows VM stress in the skin during the penetration of arrays characterized by projection densities of 20,400 proj cm$^{-2}$;

FIG. 5A is a plot of penetration depth versus application velocity; FIG. 5B is a plot of penetration depth versus piston mass; FIG. 5C is a plot of penetration depth versus array size; FIG. 5D is a plot of penetration depth versus projection density; FIG. 5E is a plot of penetration depth versus energy/projection, in which the significant Spearman correlation (p<0.0001) found between penetration depth pd and application energy per projection U was modeled with power laws pd=A U$^B$, i.e. straight (dotted) lines in Log-Log scale, horizontal error-bars represent the standard deviation of the measurement of application velocity and number of microprojections on the array following wafer dicing, and vertical error-bars were obtained as in FIG. 4B;

DETAILED DESCRIPTION OF THE PREFERRED EMBODIMENTS

In-depth understanding of skin elastic and rupture behaviors is important for next-generation biomedical devices because it enables targeted delivery of vaccines, as well as minimally-invasive extraction of diagnostic biomarkers and robotic/haptic surgery. Penetration of the skin's superficial barriers and precise targeting of strata rich in antigen-presenting cells is critical to elicit potent low-dose immunogenicity. However, the paucity of relevant skin mechanical characterization and lack of established fracture models has limited the rational design of cutaneous devices. The present invention exploits experimental and numerical studies of skin mechanics during dynamic interaction with individual and arrays of microscopic penetrators to provide improved methods and devices for delivering active agents into the skin. Micro-indentation of individual strata reveals that the hyperelastic moduli are dramatically rate-dependent, and allows extrapolation of the stiffness properties at velocity regimes (>mm s$^{-1}$) relevant for dynamically-actuated cutaneous devices. These are used to parameterize a layered finite-element (FE) representation of skin that includes a novel implementation of ductile failure. Iterative refinement to match empirical penetration assays yields characteristic fracture energies (~10 pJ μm$^{-2}$) significantly lower than previously reported (>>100 pJ μm$^{-2}$). The resulting FE simulations satisfactorily predict the penetration depth of microprojection arrays across a diverse range of designs and application conditions, and shows limited sensitivity to the parameterization choice. The knowledge and numerical tools developed provide guidelines to rationally engineer skin penetrators. Specific array design and application conditions can be developed to increase the targeting consistency across patients and minimize the penetration energy while controlling skin inflammation, tolerability and acceptability.

Both experiments and theoretical models were used to develop an understanding of the skin's mechanical properties relative to the dynamic penetration of individual and multiple microscopic penetrators. These properties are particularly relevant to the skin treatment by microneedles/microprojections for vaccine delivery as well as minimally-invasive extraction of diagnostic biomarkers. Starting from micro-indentation experiments on mouse skin (FIG. 1C), the hyperelastic properties of the epidermal and dermal layers at high strain-rates (>1 μs$^{-1}$) were derived. These were utilized in conjunction with finite-element simulations to further investigate the rate-dependent skin mechanical response to the impact of individual and arrays of penetrator tips.

Figure 4D:
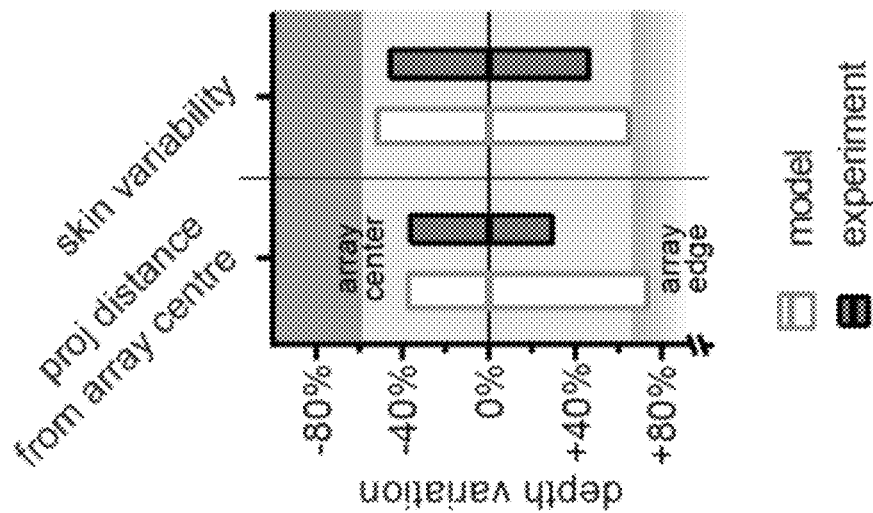
FIG. 4D is a schematic of the numerical and experimental variations of penetration depth; the depth range originating from the skin variability has been represented using the deviation of the penetration measurements across biological repeats, and compared to the widest numerical variability deriving from skin properties, i.e. skin stiffness.
Figure 4B:
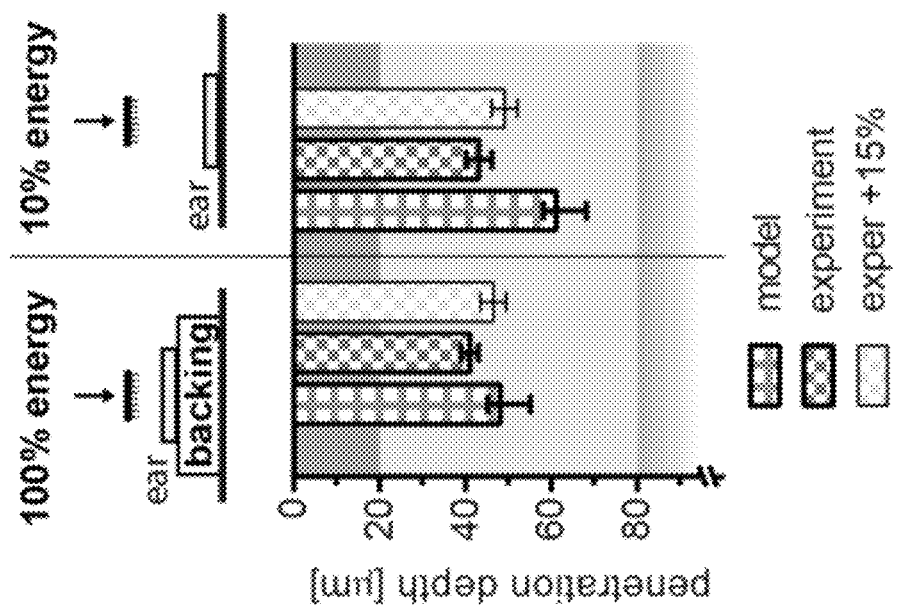
FIG. 4B is a schematic of the penetration depth resulting from standard treatment, i.e. firing the array with an energy of ~13 mJ (~35 g piston at ~0.85 m s$^{-1}$) on a PDMS-backed ear (left), and ~1.3 mJ (~5 g at ~0.75 m s$^{-1}$) on ear alone; a +15% correction factor was considered to account for the tissue shrinking due to histology treatment; the mean±se (n=4) is represented for the experimental groups, whereas the error-bars of the model group represent the uncertainty due to FE parameterization as in FIG. 4C.
Figure 4A:
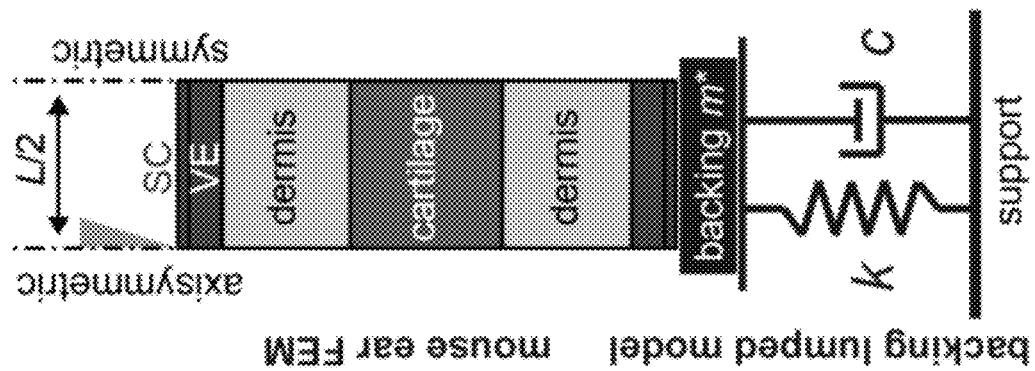
FIG. 4A is a schematic of a model used to simulate projection array penetration into skin backed by soft tissue; mouse ear layers were modeled using an axisymmetric FE geometry with a symmetric boundary; the soft backing material was modeled using a parallel spring-damper-mass lumped element.

The complete model schematized in FIG. 4A was used to simulate skin mechanical interaction with the microprojections in the conditions used for mouse vaccination experiment (G. J. P. Fernando, X. F. Chen, T. W. Prow, M. L. Crichton, E. J. Fairmaid, M. S. Roberts, I. H. Frazer, L. E. Brown, M. A. F. Kendall, PLOS One 2010, 5, e10266). Penetration was studied for varying array designs and application parameters. For validation, the calculated penetration depths were compared with experimental measurements from histological sections of skin treated with dye-coated arrays according to an established protocol (M. L. Crichton, A. Ansaldo, X. F. Chen, T. W. Prow, G. J. P. Fernando, M. A. F. Kendall, Biomaterials 2010, 31, 4562).

FIG. 4B shows the simulation and experimental results for a 4×4 mm$^2$ array containing ~3000 microprojections spaced of L=70 μm (i.e. ~ 20 kproj cm$^{-2}$) applied on PDMS-backed skin at 0.85 m s$^{-1}$ with the 35 g piston (i.e. ~ 13 mJ), the 'standard treatment' condition. The resulting penetration depth, 48 μm from the model, is in good agreement with the experimental measurement, 41±2 μm (mean±se). This simulation indicated that 6.2% of the energy is transferred to the skin. The model was revised by removing the backing and applying the array to the ear alone using (conservatively) ~10% of the energy (~5 g at ~0.75 ms$^{-1}$, i.e. ~ 1.3 mJ). FIG. 4B shows that this reduced-energy condition penetrates un-backed skin to a depth comparable with the standard treatment on backed skin, which further validates the skin and PDMS parameterizations.

The sensitivity of the numerically-derived penetration depth to the variation of the model parameters was assessed with a set of limit analyses. In brief, the standard treatment simulation was repeated assigning upper and lower boundary values to each individual parameter, one at a time. The input-parameter intervals are summarized in Table 1 and are representative of the range of FE parameters, variation of skin properties as reported in the literature and possible array design tolerances or modifications. For simple reference to FIGS. 5A-5E, the top, respectively bottom, row in Table 1 shows the condition resulting into shallower, respectively deeper, penetration.

TABLE 1

Summary of parameter variation ranges used to assess the sensitivity of the numerical solutions.

| FE mesh density | FE mass scaling [ps] | Skin elastic moduli | Skin Poisson's ratio | Skin fracture strain | Skin epider thickn [μm] | Skin dermis thickn [μm] | Skin-proj friction | Array proj location | Array coating | Array proj diamet [μm] | Array proj tip angle [deg] | Array proj tip diamet [μm] |
|---|---|---|---|---|---|---|---|---|---|---|---|---|
| −50% st$^{a)}$ | ~100 | +70% st$^{b)}$ | 0.35 | >20% | 9 | 80 | | center | yes$^{e)}$ | 29 | | 5 |
| +25%. | ~50 | | 0.45 | ≤20%$^{c)}$ | 20 | 60 | 0.4 | mean$^{d)}$ | | 23 | 30 | 1 |
| | none | −50% | 0.49 | 0% | 27 | 40 | 0.7 | edge | no | 17 | 50 | |
| | | | | | | | 0.05 | | | | 10 | | st = standard value.

Figure 4C:
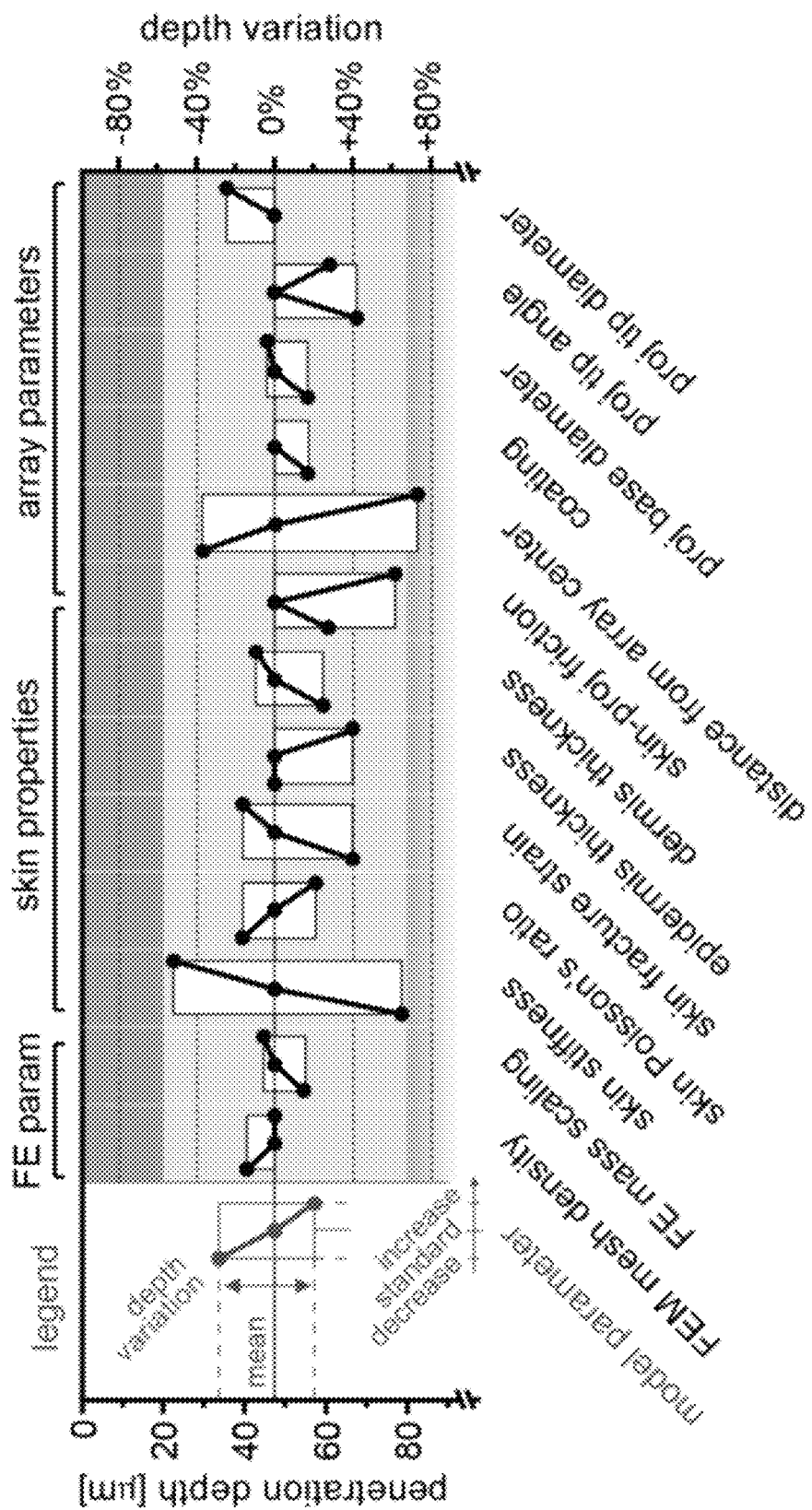
FIG. 4C is a schematic of the sensitivity of the numerical solution to model parameterization when the standard treatment condition (35 g, ~0.85 m s$^{-1}$) is used; the bars indicate the penetration depth resulting varying the model parameters; the direction of the depth change when the specific model parameter increases is indicated by the black curves.

FIG. 4C shows that no significant difference resulted after refining the mesh, which indicates that the mesh of choice is appropriate. Among other skin characteristics, penetration depth was most sensitive to strata stiffness (FIG. 4C); and, interestingly, the resulting numerical depth range is in close agreement with the measurement variation across biological repeats (FIG. 4D). On the other hand, the experiments revealed a significantly deeper penetration depth towards the edges of the array, likely due to the larger force exerted by peripheral microprojections. By scaling the microprojection momentum the increasing penetration depth caused by projections located at increasing distance from the array center could be reasonably predicted (FIG. 4D).

The penetration resulting from different array application conditions (FIGS. 5A-5B) and designs (FIGS. 5C-5D) was investigated numerically and empirically by further applying the computational and experimental methods. Increasing microprojection velocity resulted in deeper penetration due to the larger energy. Separately, lower piston masses (using the same application spring load) resulted in slightly decreasing penetration, despite the theoretically-constant application potential energy. In fact, applicator characterization revealed lower than expected application velocities for the lower masses (<35 g), possibly due to a greater friction of the lighter plastic piston against the applicator housing compared to the standard brass piston. The simulations were run using the measured velocities, rather than the theoretically-calculated ones. Decreasing the array size or the microprojection density (constant array size) resulted in deeper penetration mostly because the same application energy is shared among fewer projections. The numerical prediction and the experimental measurement were in reasonable agreement. Specifically, the model appears to overestimate the depth especially when the projections are widely spaced and approach the deep dermis. This is possibly due to two reasons: 1) the deeper penetration of the peripheral projections (FIG. 4D) might allow contact between the SC and the base of the array, especially for sparse arrays; and 2) the projection interacts with the cartilage, which mechanical properties were not accurately established.

Figure 5B:
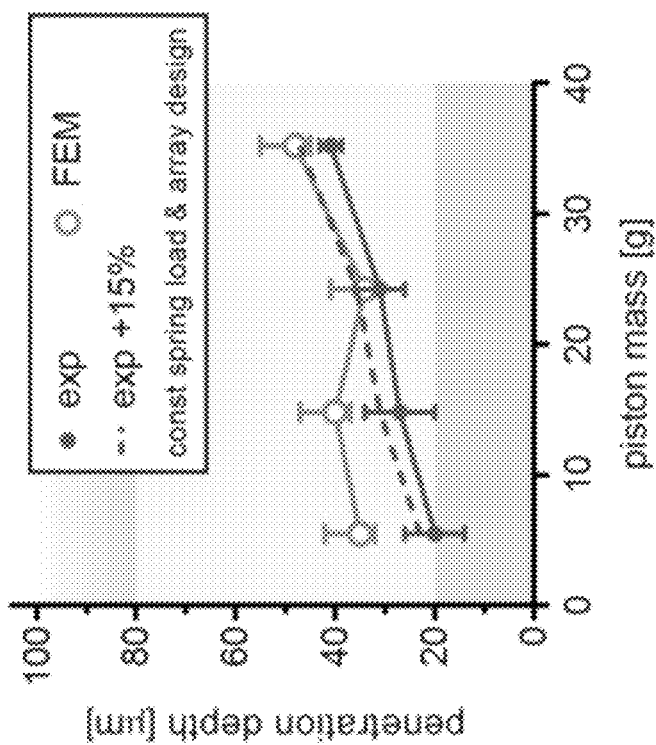
FIGS. 5A-5E are plots of numerical (FEM result±FE error) and experimental (exp mean±se) penetration depths as a function of varying application conditions and array designs.
Figure 5A:
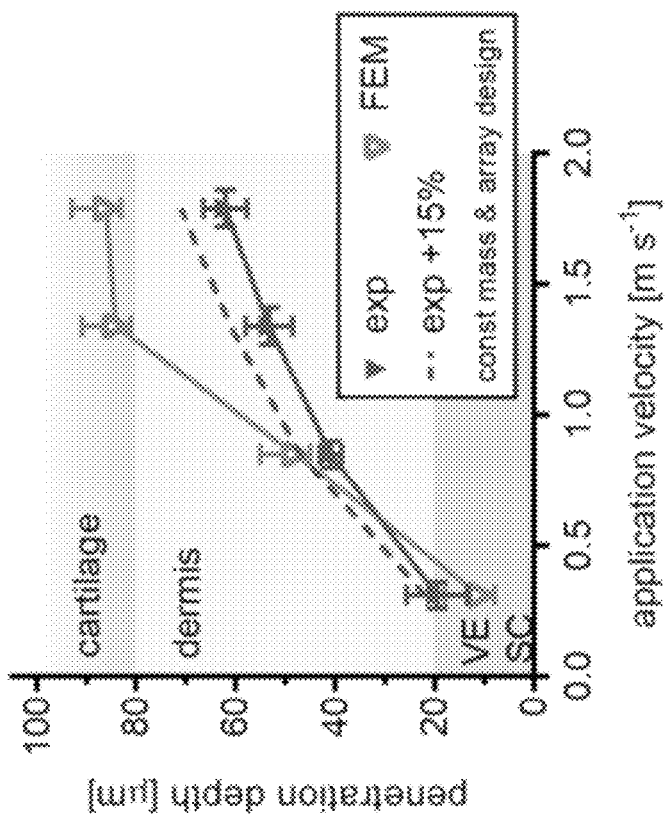
Figure 5D:
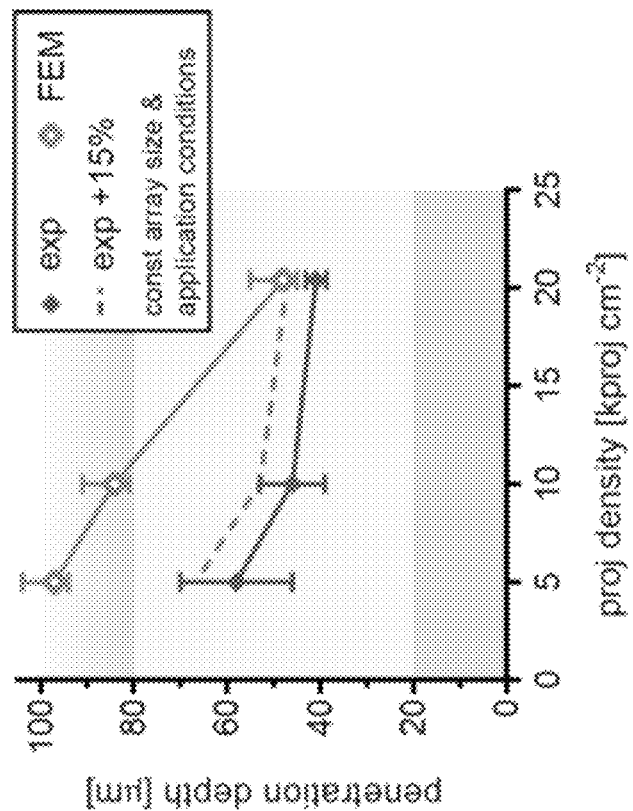
Figure 5C:
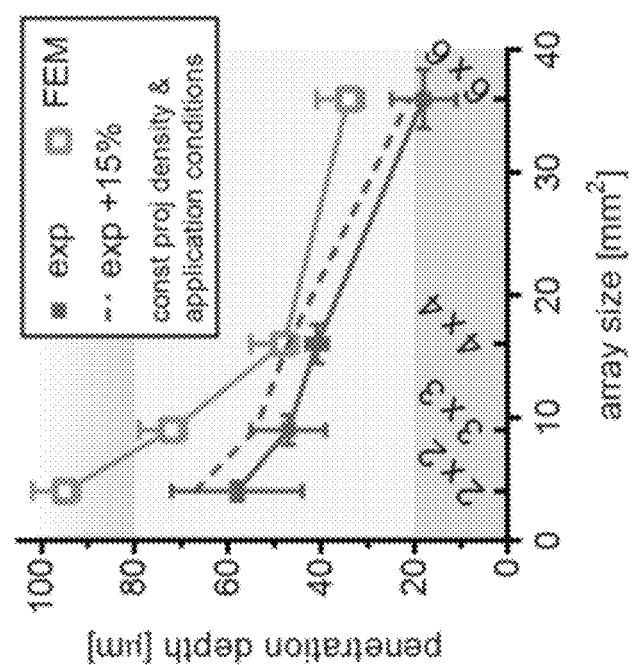
Figure 5F:
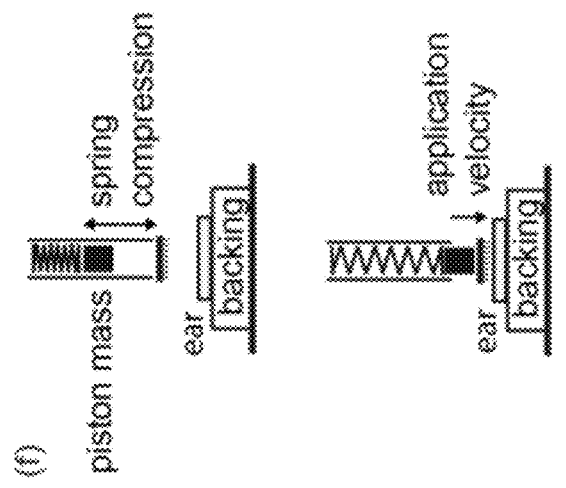
FIG. 5F is a schematic representation of applicator function and main parameters.
Figure 5E:
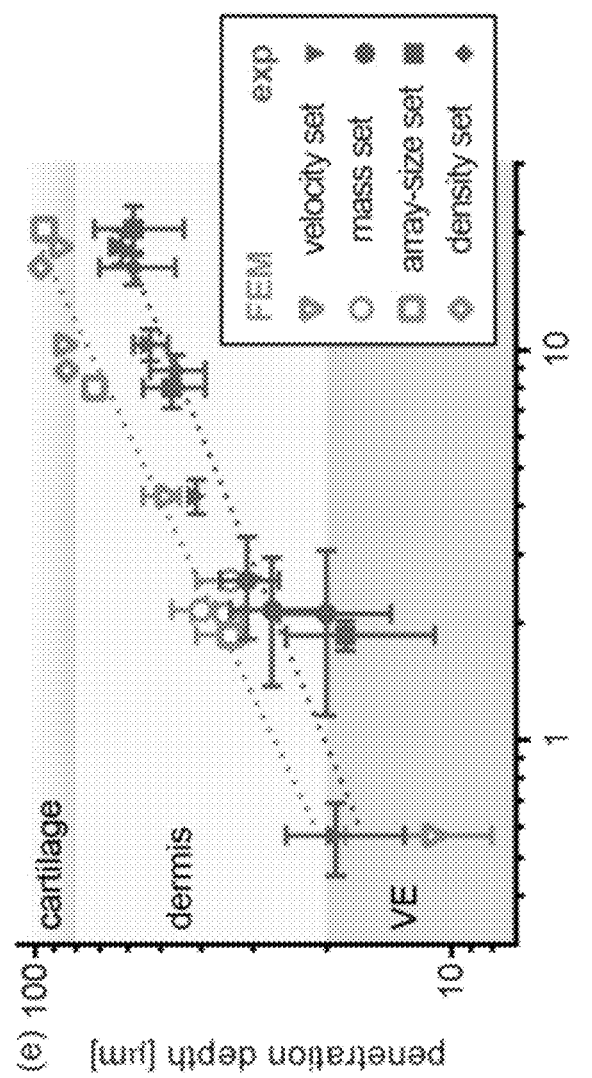

There is significant Spearman correlation (p<0.0001) between the penetration depth pd and the application energy per projection U (FIG. 5E). The power $(1.30+0.04)$ $U^{(0.38=0.04)}$ (mean±se) fitted the experimental data satisfactorily ($R^2$=0.931). An analogous non-linear regression for the numerical dataset yielded $(1.43+0.05)$ $U^{(0.44=0.05)}$ with similar goodness-of-fit ($R^2$=0.932). These curves pd=A $U^B$ appear as straight lines in Log-Log scale (FIG. 5E) where A is the intercept, B is the slope, the depth pd is measured in μm and (in μJ. FIG. 5E also suggests that the penetration depth of arrays with custom design and application conditions can be simplistically predicted from the application energy (per projection) using this empirical relationship.

Figure 6B:
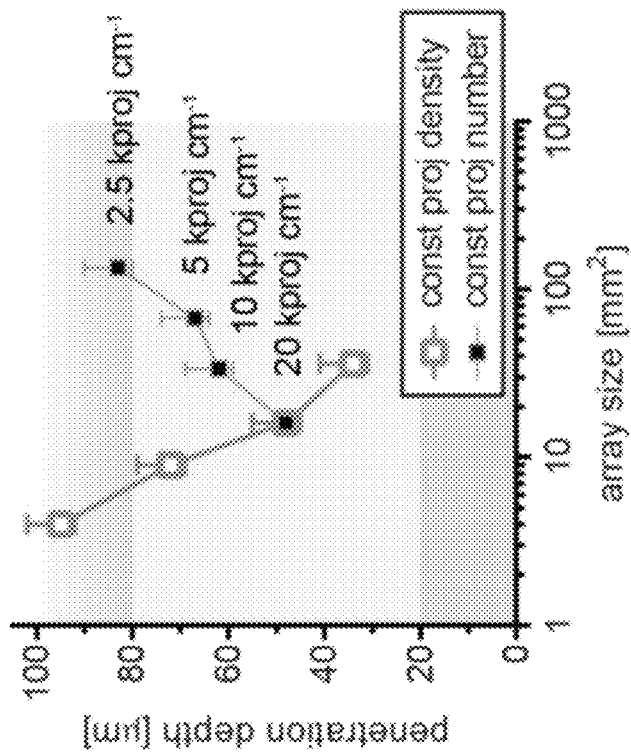
FIG. 6B is a plot of penetration depth versus array size under conditions where 1) constant projection density and 2) constant projection number.
Figure 6A:
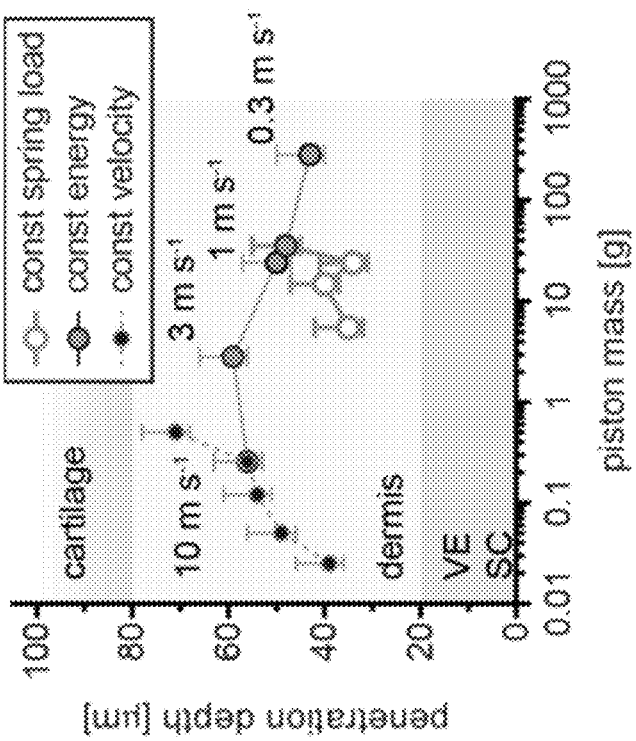
FIG. 6A is a plot of penetration depth versus piston mass under conditions where 1) constant spring load; 2) constant energy and 3) constant velocity.
Figure 6C:
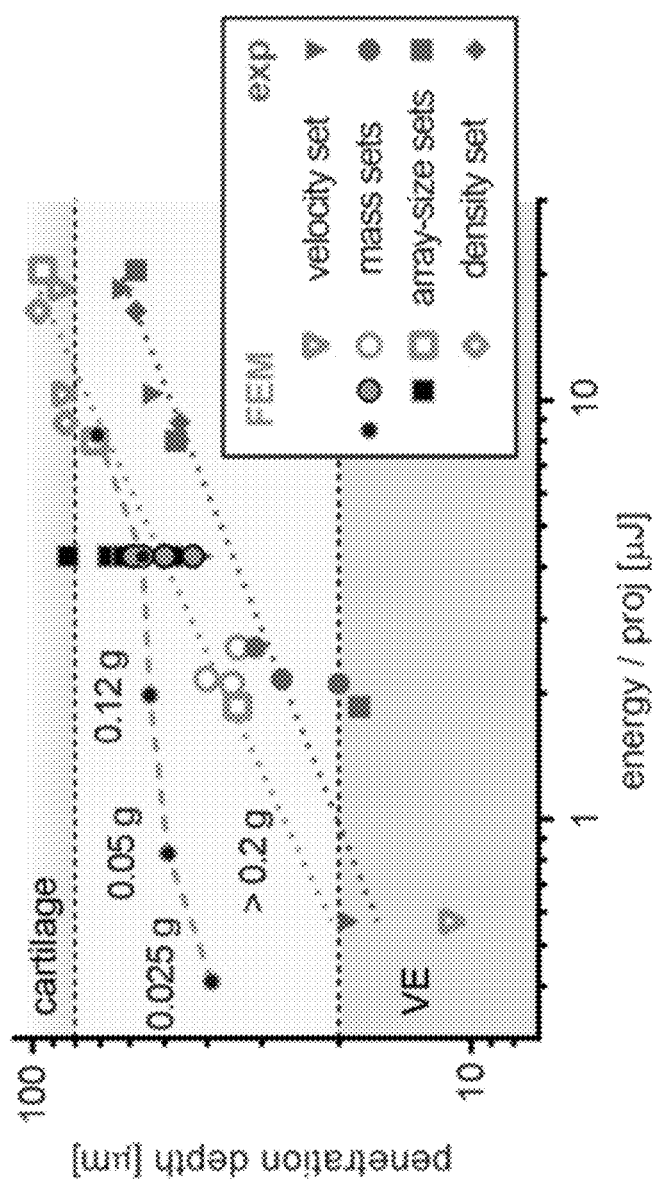
FIG. 6C is a plot of penetration depth versus energy/projection comparing experimental and FEM for velocity sets, mass sets, array-size-sets and density sets, in which the penetration depth escapes the Log-Log linear dependence with application energy per projection for very low piston masses and large array sizes; error-bars were omitted for clarity.
Figure 6E:
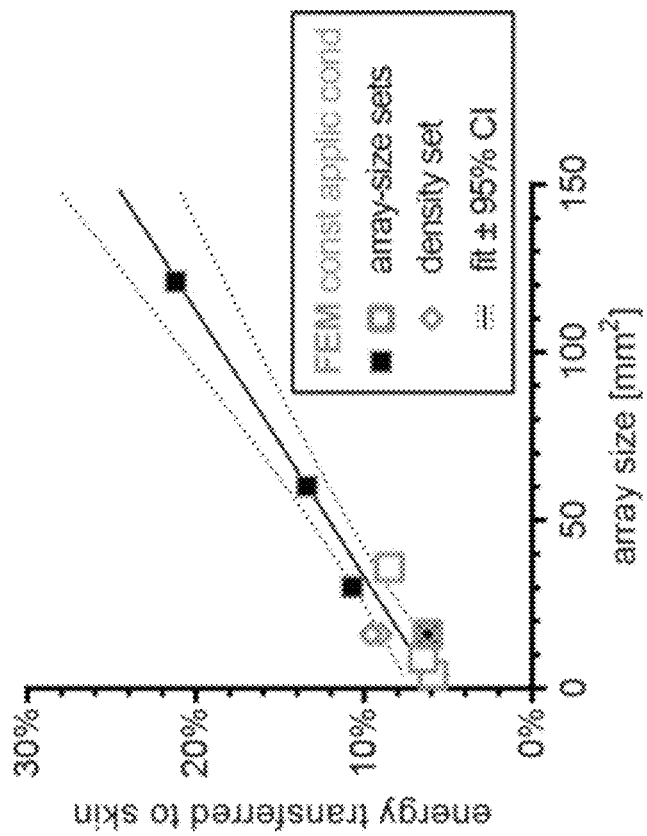
FIG. 6E is a plot of the percentage of application energy transferred to the skin versus array size.
Figure 6D:
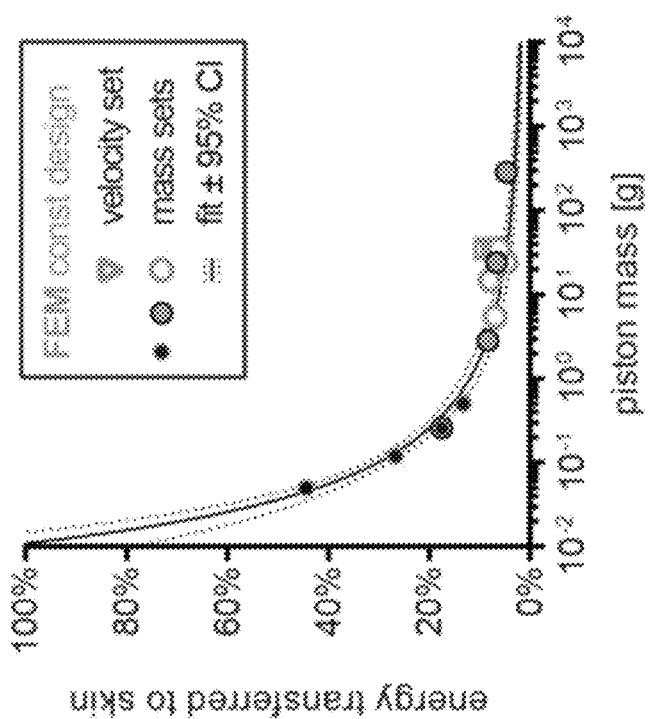
FIG. 6D is a plot of the percentage of application energy transferred to the skin versus piston mass.

The computational model was applied to investigate alternative designs and application conditions and challenge the trend of FIG. 5E. Interestingly, decreasing piston mass (FIG. 6A) or increasing the array size (FIG. 6B) resulted in increased penetration depth although the energy per projection was held constant. These conditions, as well as 10 m s$^{-1}$ applications for masses below 0.2 g (FIG. 6A) markedly violated the Log-Log linear relationship between depth and energy per projection (FIG. 6C). Specifically, the results indicate that isoenergetic applications achieve a ~2-fold deeper penetration using a mass <0.05 g or spreading the microprojections over a 10-fold larger area. Equivalently, the energy required to reach a mid-dermal depth (~50 μm) can be reduced by over 80% by lowering the mass from 35 g to 0.05 g. Key for this 'energy sparing' phenomenon is the increasing application velocity required to maintain a constant energy while decreasing the mass. In fact, the simulations of velocities <3 ms$^{-1}$ showed that skin fracture starts after a large compression of the backing and terminates after 0.5-1 ms. In contrast, the fracture process is completed in ~10 us at 10 m s$^{-1}$, before the backing has started to deform. Likely, these different penetration regimes arise because the projection motion competes with the transmission of the deformation to the backing through the stress waves. Such behavior suggests that an efficiency around 55% can be theoretically achieved by reducing the moving mass down to the array itself (~0.03 g). In addition, the energy transfer efficiency linearly correlated with array size (FIG. 6E; Pearson's r=0.966, p<0.0001, slope=(0.126+0.013)% mm$^{-2}$, intercept=(5.78+0.62)%). This is likely to be because distributing the impact over a larger surface increases the overall backing elastic force response, thus results in an effectively stiffer substrate.

The results of FIGS. 6A-6E indicate that penetration depth is not a unique function of the energy per projection. Rather, the application energy required to target a specific depth can be modulated by varying the velocity-to-mass ratio. This represents an important degree of freedom to seek immunologically-beneficial levels of inflammation (e.g. cell stress/death via mechanical perturbation) without compromising treatment tolerability and acceptability by the patient. On the other hand, high-velocity, low-mass applications allow the microprojections to interact mainly with the superficial layers (i.e. the skin). This effectively reduces the dependence of penetration on the skin backing properties, hence potentially improves the targeting consistency across patients with different subcutaneous tissue composition (e.g. different body-mass index).

The skin dynamic behavior is the main cause of such a diverse mechanical response. Firstly, the heterogeneous layered composition favored fracture in the early impact stages for large application velocities. Specifically, the stress was effectively retained at the surface due to the slow stress-wave propagation of the deep strata (cartilage, PDMS, fat or muscle), comparatively lower in stiffness. Secondly, the equivalent strain required to initiate failure (i.e. meet the yield criterion) decreased with increasing velocity because skin elasticity (i.e. the stress response to a specific strain) has a steeper rate-dependent increase compared to the yield strength. As a consequence, penetration is more difficult in quasi-static conditions, as the Young's modulus-to-yield strength ratio decreases below 1, due to the resulting strata softness (compliance).

The resulting penetration model satisfactorily reproduced the experimental behavior for a wide range of conditions, and further proved robust to variations in parameterization. However, the utilized elastic moduli were derived from indentations using constant probe velocity, and are relative to the peak strain rates at impact. Hypothetically, the resulting skin stress relaxation should result in lower penetration depths that match the experimental measurements more closely.

While significant differences in skin behavior are expected if the dynamic regime is changed (e.g. from impact to quasi-static or vibratory application), penetration of other microneedle array designs (typically characterized by sparser, larger penetrators) will likely follow the trends showed in FIGS. 5A-5E and FIGS. 6A-6E. This is justified by the low variation between the relative energetic contributions (e.g. fracture, deformation and friction) (FIG. 3G) and the approximately constant stress generated as tip radius and spacing increase. As can be seen in FIGS. 4A-4D a variety of parameters may affect the depth of penetration of microprojections into the skin: skin stiffness, skin fracture strain, epidermis thickness, dermis thickness, skin-microprojection friction, distance of projections from the array center, amount of coating on microprojection, microprojection tip angle, microprojection shape, velocity of microprojection array into the skin, mass of microprojection array, velocity to mass ratio of the microprojection area, area of the microprojection array, density of microprojection array, backing used behind skin target.

When administered to the skin the microprojection array may have a velocity which is greater than about 5 m/s or about 6 m/s, or about 7 m/s, or about 8 m/s, or about 9 m/s, or about 10 m/s, or about 15 m/s, or about 20 m/s, or about 25 m/s, or about 30 m/s, or about 40 m/s, or about 45 m/s, or about 50 m/s, or about 55 m/s. When administered to the skin the microprojection array may have a velocity which is about 5 m/s to about 50 m/s, or from about 5 m/s to about 45 m/s, or from 5 m/s to about 40 m/s, or from about 5 m/s to about 35 m/s, or from 5 m/s to about 30 m/s, or from 5 m/s to about 25 m/s, or from about 5 m/s to about 20 m/s, or from about 5 m/s to about 15 m/s, or from 5 m/s to about 10 m/s, or from about 10 m/s to about 50 m/s, or from about 10 m/s to about 45 m/s, or from 10 m/s to about 40 m/s, or from about 10 m/s to about 35 m/s, or from about 10 m/s to about 30 m/s, or from 10 m/s to about 25 m/s, or from about 10 m/s to about 20 m/s, or from about 10 m/s to about 15 m/s, or from about 15 m/s to about 50 m/s, or from about 15 m/s to about 45 m/s, or from 15 m/s to about 40 m/s, or from about 15 m/s to about 35 m/s, or from 15 m/s to about 30 m/s, or from 15 m/s to about 25 m/s, or from about 15 m/s to about 20 m/s, or from about 20 m/s to about 50 m/s, or from 20 m/s to about 45 m/s, or from about, or from 20 m/s to about 40 m/s, or from about 20 m/s to about 35 m/s, or from about 20 m/s to about 30 m/s, or from about 20 m/s to about 25 m/s, or from about 25 m/s to about 50 m/s, or from about 25 m/s to about 45 m/s, or from 25 m/s to about 40 m/s, or from about 25 m/s to about 35 m/s, or from about 25 m/s to about 30 m/s, or from about 30 m/s to about 50 m/s, or from about 30 m/s to about 45 m/s, or from about 30 m/s to about 40 m/s, or from about 30 m/s to about 35 m/s.

The microprojection arrays may have a mass of less than 1 gram, or less than 0.9 grams, or less than 0.8 grams, or less than 0.7 grams, or less than 0.6 grams, or less than 0.5 grams, or less than 0.6 grams, or less than 0.5 grams, or less than 0.4 grams, or less than 0.3 grams, or less than 0.2 grams, or less than 0.1 grams, or less than 0.05 grams, or less than 0.01 grams, or less than 0.005 grams, or less than 0.001 grams. The microprojection array may have a mass of from about 0.001 grams to about 5 grams of about 0.001 grams to about 2 grams, or from about 0.001 grams to about 1.5 grams, or from about 0.001 grams to about 1.0 grams, or from about 0.001 grams to about 0.9 grams, or from about 0.001 grams to about 0.8 grams, or from about 0.001 grams to about 0.7 grams, or from about 0.001 grams to about 0.6 grams, or from about 0.001 grams to about 0.5 grams, or from about 0.001 grams to about 0.4 grams, or from about 0.001 grams to about 0.3 grams, or from about 0.001 grams to about 0.2 grams, or from about 0.001 grams to about 0.1 grams from about 0.01 grams to about 5 grams of about 0.01 grams to about 2 grams, or from about 0.01 grams to about 1.5 grams, or from about 0.01 grams to about 1.0 grams, or from about 0.01 grams to about 0.9 grams, or from about 0.01 grams to about 0.8 grams, or from about 0.01 grams to about 0.7 grams, or from about 0.01 grams to about 0.6 grams, or from about 0.01 grams to about 0.5 grams, or from about 0.01 grams to about 0.4 grams, or from about 0.01 grams to about 0.3 grams, or from about 0.01 grams to about 0.2 grams, or from about 0.01 grams to about 0.1 grams, or from about 0.05 grams to about 5 grams of about 0.05 grams to about 2 grams, or from about 0.05 grams to about 1.5 grams, or from about 0.05 grams to about 1.0 grams, or from about 0.05 grams to about 0.9 grams, or from about 0.05 grams to about 0.8 grams, or from about 0.05 grams to about 0.7 grams, or from about 0.05 grams to about 0.6 grams, or from about 0.05 grams to about 0.5 grams, or from about 0.05 grams to about 0.4 grams, or from about 0.05 grams to about 0.3 grams, or from about 0.05 grams to about 0.2 grams, or from about 0.05 grams to about 0.1 grams, or from about 0.1 grams to about 1.0 grams, or from about 0.1 grams to about 5 grams, or from about 0.1 grams to about 2 grams, or from about 0.1 grams to about 0.9 grams, or from about 0.1 grams to about 0.8 grams, or from about 0.1 grams to about 0.7 grams, or from about 0.1 grams to about 0.6 grams, or from about 0.1 grams to about 0.5 grams, or from about 0.1 grams to about 0.4 grams, or from about 0.1 grams to about 0.3 grams, or from about 0.1 grams to about 0.2 grams.

The density of the microprojection on the microprojection arrays may be about 2000 microprojections/$cm^2$, or about 2500 microprojections/$cm^2$, or about 3000 microprojections/$cm^2$, or about 3500 microprojections/$cm^2$, or about 4000 microprojections/$cm^2$, or about 4500 microprojections/$cm^2$, or about 5000 microprojections/$cm^2$, or about 5500 microprojections/$cm^2$, or about 6000 microprojections/$cm^2$, or about 6500 microprojections/$cm^2$, or about 7000 microprojections/$cm^2$, or about 7500 microprojections/$cm^2$, or about 8000 microprojections/$cm^2$, or about 8500 microprojections/$cm^2$, or about 9000 microprojections/$cm^2$, or about 9500 microprojections/$cm^2$, or about 10000 microprojections/$cm^2$, or about 11000 microprojections/$cm^2$, or about 12000 microprojections/$cm^2$, or about 13000 microprojections/$cm^2$, or about 14000 microprojections/$cm^2$, or about 15000 microprojections/$cm^2$, or about 16000 microprojections/$cm^2$, or about 17000 microprojections/$cm^2$, or about 18000 microprojections/$cm^2$, or about 19000 microprojections/$cm^2$, or about 20000 microprojections/$cm^2$. The density of the microprojection on the microprojection arrays may be from about 2000 to about 20000 microprojections/$cm^2$, or from about 2000 to about 15000 microprojections/$cm^2$, or from about to about 10000 microprojections/$cm^2$, or from about 2000 to about 9000 microprojections/$cm^2$, or from about 2000 to about 8000 microprojections/$cm^2$, or from about 2000 to about 7500 microprojections/$cm^2$, or from about 2000 to about 7000 microprojections/$cm^2$, or from about 2000 to about 6000 microprojections/$cm^2$, or from about 2000 to about 5000 microprojections/$cm^2$, or from about 2000 to about 4000 microprojections/$cm^2$, or from about 3000 to about 20000 microprojections/$cm^2$, or from about 3000 to about 15000 microprojections/$cm^2$, or from about to about 10000 microprojections/$cm^2$, or from about 3000 to about 9000 microprojections/$cm^2$, or from about 3000 to about 8000 microprojections/$cm^2$, or from about 3000 to about 7500 microprojections/$cm^2$, or from about 3000 to about 7000 microprojections/$cm^2$, or from about 3000 to about 6000 microprojections/$cm^2$, or from about 3000 to about 5000 microprojections/$cm^2$, or from about 3000 to about 4000 microprojections/$cm^2$, or from about 4000 to about 20000 microprojections/$cm^2$, or from about 4000 to about 15000 microprojections/$cm^2$, or from about to about 10000 microprojections/$cm^2$, or from about 4000 to about 9000 microprojections/$cm^2$, or from about 4000 to about 8000 microprojections/$cm^2$, or from about 4000 to about 7500 microprojections/$cm^2$, or from about 4000 to about 7000 microprojections/$cm^2$, or from about 4000 to about 6000 microprojections/$cm^2$, or from about 4000 to about 5000 microprojections/$cm^2$, or from about 5000 to about 20000 microprojections/$cm^2$, or from about 5000 to about 15000 microprojections/$cm^2$, or from about to about 10000 microprojections/$cm^2$, or from about 5000 to about 9000 microprojections/$cm^2$, or from about 5000 to about 8000 microprojections/$cm^2$, or from about 5000 to about 7500 microprojections/$cm^2$, or from about 5000 to about 7000 microprojections/$cm^2$, or from about 5000 to about 6000 microprojections/$cm^2$.

At least a portion of the projections may be coated. Accordingly, one way of providing material for delivery to the biological subject is by providing the material within the coating. For example, the coating may include a vaccine for providing an immunological response within the subject. The coating may be provided in liquid or non-liquid forms, and may further include ingredients other than the material to be delivered, such as an adjuvant. Suitable coating formulations for use with projections patches and methods of applying such coatings to the projections are known, as described, for example, in WO/2010/042996 and WO/2009/079712.

Although any type of coating may be used, particularly advantageous embodiments of the microprojection arrays are provided with at least a portion of the projections coated with a non-liquid coating. In this regard, the term "non-liquid" coating will be understood to include a coating that is applied in a liquid form and allowed to dry or otherwise solidify to thereby form a non-liquid coating.

The non-liquid coating may act as an additional substantially solid layer of material which can be used to even further adjust the geometry of the projections by optionally causing the projections to have an effective profile of a different shape to the underlying uncoated profile of the projections as initially fabricated.

The microprojections of the array of the present invention may be of any shape including cylindrical or conical. Other geometries are also possible. The microprojection arrays may have substrate with a plurality of microprojections protruding from the substrate wherein the microprojections have a tapering hexagonal shape and comprise a tip and a base wherein the base has two substantially parallel sides with a slight draught angle of approximately 1 to 20 degrees up to a transition point at which point the angle increases to from about 20 degrees to about 70 degrees. A sharp blade-like tip will allow for enhanced penetration of the microprojections into the skin while also generating an enhanced localized cell death/bystander interaction in the skin with a different profile than conical microprojection arrays. The sharp blade-like tips of the microprojections may also increase the level of danger signals and antigen to more live cells thereby increasing the physical adjuvant effect of microprojections and thereby improving immune responses. The tip of the microprojections of the present invention may have a width of about 0.5 µm, or about 1.0 µm, or about 1.5 µm, or about 2.0 µm, or about 2.5 µm, or about 3.0 µm, or about 3.5 µm, or about 4.0 µm, or about 4.5 µm, or about 5.0 µm. The tip of the microprojections of the present invention may have a width of from about 0.5 µm to about 5.0 µm, or from about 0.5 µm to about 4.5 µm, or from about 0.5 µm to about 4.0 µm, or from about 0.5 µm to about 3.5 µm, or from about 0.5 µm to about 3.0 µm, or from about 0.5 µm to about 2.5 µm, or from about 0.5 µm to about 2.0 µm, or from about 0.5 µm to about 1.5 µm, or from about 0.5 µm to about 1.0 µm, or from about 1.0 µm to about 5.0 µm, or from about 1.0 µm to about 4.5 µm, or from about 1.0 µm to about 4.0 µm, or from about 1.0 µm to about 3.5 µm, or from about 1.0 µm to about 3.0 µm, or from about 1.0 µm to about 2.5 µm, or from about 1.0 µm to about 2.0 µm, or from about 1.0 µm to about 1.5 µm, or from about 1.5 µm to about 5.0 µm, or from about 1.5 µm to about 4.5 µm, or from about 1.5 µm to about 4.0 µm, or from about 1.5 µm to about 3.5 µm, or from about 1.5 µm to about 3.0 µm, or from about 1.5 µm to about 2.5 µm, or from about 1.5 µm to about 2.0 µm, or from about 2.0 µm to about 5.0 µm, or from about 2.0 µm to about 4.5 µm, or from about 2.0 µm to about 4.0 µm, or from about 2.0 µm to about 3.5 µm, or from about 2.0 µm to about 3.0 µm, or from about 2.0 µm to about 2.5 µm, or from about 2.5 µm to about 5.0 µm, or from about 2.5 µm to about 4.5 µm, or from about 2.5 µm to about 4.0 µm, or from about 2.5 µm to about 3.5 µm, or from about 2.5 µm to about 3.0 µm.

The microprojection array when applied to the skin may have a mass-to-velocity ratio of less than about 0.0005 g/m/s, or less than about 0.001 g/m/s/or less than about 0.002 g/m/s, or less than about 0.003 g/m/s, or less than about 0.004 g/m/s/or less than about 0.005 g/m/s, or less than about 0.006/m/s, or less than about 0.007 g/m/s/or less than about 0.008 g/m/s, or less than about 0.009 g/m/s, or less than about 0.01 g/m/s/or less than about 0.02 g/m/s, or less than about 0.03/m/s, or less than about 0.04 g/m/s/or less than about 0.05 g/m/s, or less than about 0.06 g/m/s, or less than about 0.07 g/m/s/or less than about 0.08 g/m/s, or less than about 0.09/m/s, or less than about 0.10 g/m/s/or less than about 0.20 g/m/s, or less than about 0.30 g/m/s, or less than about 0.40 g/m/s/or less than about 0.50 g/m/s. The microprojection array when applied to the skin may have a mass-to-velocity ratio of about 0.0005 g/m/s to about 0.50 g/m/s, or from about 0.0005 g/m/s to about 0.40 g/m/s, or from about 0.0005 g/m/s to about 0.30 g/m/s, or from about 0.0005 g/m/s to about 0.20 g/m/s, or from about 0.0005 g/m/s to about 0.10 g/m/s, or from about 0.0005 g/m/s to about 0.009 g/m/s, or from of about 0.0005 g/m/s to about 0.008 g/m/s, or from about 0.0005 g/m/s to about 0.007 g/m/s, or from about 0.0005 g/m/s to about 0.006 g/m/s, or from about of about 0.0005 g/m/s to about 0.005 g/m/s, or from about 0.0005 g/m/s to about 0.004 g/m/s, or from about 0.0005 g/m/s to about 0.003 g/m/s, or from about of about 0.0005 g/m/s to about 0.002 g/m/s, or from about 0.0005 g/m/s to about 0.001 g/m/s, or from about 0.001 g/m/s to about 0.50 g/m/s, or from about 0.001 g/m/s to about 0.40 g/m/s, or from about 0.001 g/m/s to about 0.30 g/m/s, or from about 0.001 g/m/s to about 0.20 g/m/s, or from about 0.001 g/m/s to about 0.10 g/m/s, or from about 0.001 g/m/s to about 0.009 g/m/s, or from of about 0.001 g/m/s to about 0.008 g/m/s, or from about 0.001 g/m/s to about 0.007 g/m/s, or from about 0.001 g/m/s to about 0.006 g/m/s, or from about of about 0.001 g/m/s to about 0.005 g/m/s, or from about 0.001 g/m/s to about 0.004 g/m/s, or from about 0.001 g/m/s to about 0.003 g/m/s, or from about of about 0.001 g/m/s to about 0.002 g/m/s, or from about 0.005 g/m/s to about 0.50 g/m/s, or from about 0.005 g/m/s to about 0.40 g/m/s, or from about 0.005 g/m/s to about 0.30 g/m/s, or from about 0.005 g/m/s to about 0.20 g/m/s, or from about 0.005 g/m/s to about 0.10 g/m/s, or from about 0.005 g/m/s to about 0.009 g/m/s, or from of about 0.005 g/m/s to about 0.008 g/m/s, or from about 0.005 g/m/s to about 0.007 g/m/s, or from about 0.005 g/m/s to about 0.006 g/m/s, or from about 0.033 g/m/s to about 0.0008 g/m/s.

The area of the microprojection arrays in area may be between about 10 $mm^2$ to about 1000 $mm^2$, or from about 10 $mm^2$ to about 900 $mm^2$, or from about 10 $mm^2$ to about 800 $mm^2$, or from about 10 $mm^2$ to about 700 $mm^2$, or from about 10 $mm^2$ to about 600 $mm^2$, or from about 10 $mm^2$ to about 600 $mm^2$, or from about 10 $mm^2$ to about 500 $mm^2$, or from about 10 $mm^2$ to about 400 $mm^2$, or from about 10 $mm^2$ to about 300 $mm^2$, or from about 10 $mm^2$ to about 200 $mm^2$, or from about 10 $mm^2$ to about 100 $mm^2$, or from about 10 $mm^2$ to about 90 $mm^2$, or from about 10 $mm^2$ to about 80 $mm^2$, or from about 10 $mm^2$ to about 70 $mm^2$, or from about 10 $mm^2$ to about 60 $mm^2$, or from about 10 $mm^2$ to about 50 $mm^2$, or from about 10 $mm^2$ to about 40 $mm^2$, or from about 10 $mm^2$ to about 30 $mm^2$, or from about 10 $mm^2$ to about 20 $mm^2$, or from about 20 $mm^2$ to about 1000 $mm^2$, or from about 20 $mm^2$ to about 900 $mm^2$, or from about 20 $mm^2$ to about 800 $mm^2$, or from about 20 $mm^2$ to about 700 $mm^2$, or from about 10 $mm^2$ to about 600 $mm^2$, or from about 20 $mm^2$ to about 500 $mm^2$, or from about 20 $mm^2$ to about 400 $mm^2$, or from about 20 $mm^2$ to about 300 $mm^2$, or from about 20 $mm^2$ to about 200 $mm^2$, or from about 20 $mm^2$ to about 100 $mm^2$, or from about 20 $mm^2$ to about 90 $mm^2$, or from about 20 $mm^2$ to about 80 $mm^2$, or from about 20 $mm^2$ to about 70 $mm^2$, or from about 20 $mm^2$ to about 60 $mm^2$, or from about 20 $mm^2$ to about 50 $mm^2$, or from about 20 mm² to about 40 mm², or from about 20 mm² to about 30 mm², or from about 30 mm² to about 1000 mm², or from about 30 mm² to about 900 mm², or from about 30 mm² to about 800 mm², or from about 30 mm² to about 700 mm², or from about 10 mm² to about 600 mm², or from about 30 mm² to about 500 mm², or from about 30 mm² to about 400 mm², or from about 30 mm² to about 300 mm², or from about 30 mm² to about 200 mm², or from about 30 mm² to about 100 mm², or from about 30 mm² to about 90 mm², or from about 30 mm² to about 80 mm², or from about 30 mm² to about 70 mm², or from about 30 mm² to about 60 mm², or from about 30 mm² to about 50 mm², or from about 30 mm² to about 40 mm², or from about 40 mm² to about 1000 mm², or from about 40 mm² to about 900 mm², or from about 40 mm² to about 800 mm², or from about 40 mm² to about 700 mm², or from about 10 mm² to about 600 mm², or from about 40 mm² to about 500 mm², or from about 40 mm² to about 400 mm², or from about 40 mm² to about 400 mm², or from about 40 mm² to about 200 mm², or from about 40 mm² to about 100 mm², or from about 40 mm² to about 90 mm², or from about 40 mm² to about 80 mm², or from about 40 mm² to about 70 mm², or from about 40 mm² to about 60 mm², or from about 40 mm² to about 50 mm², or from about 50 mm² to about 1000 mm², or from about 50 mm² to about 900 mm², or from about 50 mm² to about 800 mm², or from about 50 mm² to about 700 mm², or from about 10 mm² to about 600 mm², or from about 50 mm² to about 500 mm², or from about 50 mm² to about 400 mm², or from about 50 mm² to about 300 mm², or from about 50 mm² to about 200 mm², or from about 50 mm² to about 100 mm², or from about 50 mm² to about 90 mm², or from about 50 mm² to about 80 mm², or from about 50 mm² to about 70 mm², or from about 50 mm² to about 60 mm², or from about 60 mm² to about 1000 mm², or from about 60 mm² to about 900 mm², or from about 60 mm² to about 800 mm², or from about 60 mm² to about 700 mm², or from about 10 mm² to about 600 mm², or from about 60 mm² to about 500 mm², or from about 60 mm² to about 400 mm², or from about 60 mm² to about 300 mm², or from about 60 mm² to about 600 mm², or from about 60 mm² to about 100 mm², or from about 60 mm² to about 90 mm², or from about 60 mm² to about 80 mm², or from about 60 mm² to about 70 mm², or from about 16 mm² to about 400 mm², or from about 36 mm² to about 225 mm², or from about 64 mm² to about 100 mm²

The microprojections of the microprojection arrays of the present invention may be solid or non-porous or contain hollow portions therein. In some embodiments the microprojection as solid and non-porous and do not contain hollow portion therein. In preferred embodiments the devices of the present invention do not contain reservoirs.

In view of the above, it will be appreciated that the present invention is generally directed to devices and methods for intradermal delivery of active agents into the skin. The invention is directed to devices and methods for improving the immunogenicity of vaccine preparations by intradermal delivery of the vaccine via a microprojection array in which the parameters for delivery of the active agents have been developed to achieve appropriate depth penetration and efficient delivery of the active agent.

The methods of the present invention may be used to design vaccination devices as well as develop the parameters for delivery of vaccines efficiently and minimize the penetration energy of the array while controlling skin inflammation, tolerability and acceptability. The present methods further enable investigation of the application of other cutaneous devices (e.g. solid, hollow, or dissolvable penetrators of custom size, possibly arranged in linear, rectangular or round arrays of arbitrary density) to different skin types.

The present invention relates to microprojection arrays wherein the physical parameters of the arrays such as but not limited to array mass, microprojection density, microprojection diameter, array size, microprojection tip angle, microprojection base diameter are determined for a given application.

The present invention relates to microprojection arrays wherein the physical parameters of the arrays can be determined for a given penetration depth range.

The present invention relates to methods of designing the physical parameters of microprojection arrays for a given penetration depth range.

EXAMPLES

Example 1

Microprojection Array Application to Mouse Skin

Microprojection arrays were fabricated using a deep-reactive ion etching approach and diced from silicon wafers by the Australian National Fabrication Facility (ANFF) at The University of Queensland as previously described (D. Jenkins, S. Corrie, C. Flaim, M. Kendall, RSC Advances 2012, 2, 3490). Arrays were first cleaned in 70% ethanol for 10 min, flushed with an excess of water, then dried under ambient conditions. Prior application to skin, the arrays were coated with fluorescent nanoparticles (Fluospheres®, 0.2 mm, Yellow Green Fluorescent 505/515 nm, 2% Solids, Molecular Probes®, Oregon, USA) as described by Coffey et al (J. W. Coffey, S. R. Corrie, M. A. Kendall, Biomaterials 2013, 34, 9572). In brief, 8 µL of solution containing Fluospheres® with 0.2% solids and 1% methylcellulose (w/v methylcellulose, Sigma-Aldrich, USA) was deposited onto a 4×4 mm² array and dried using a rotating nitrogen jet to evenly distribute the solution on the whole array while simultaneously localizing the respective payload on the projection (X. Chen, T. W. Prow, M. L. Crichton, D. W. Jenkins, M. S. Roberts, I. H. Frazer, G. J. Fernando, M. A. Kendall, J Control Release 2009, 139, 212). The volume was 4.5 µL and 18 µL for the 3×3 mm² and 6×6 mm² arrays, respectively, to maintain a constant coating volume per unit array area. Coated arrays were stored in sealed Petri dishes protected from light until used. Scanning electron Microscopy (SEM) was performed before and after coating to ensure microprojection integrity and shape consistency. The arrays selected measured (uncoated) 90-110 µm in length, 16-20 µm in width at the base, and tapered a 15°-25° angle terminating in a tip of ~1 µm in diameter. Coating increased base width increase of ~4 µm and the tip angle to ~35°. Female BALB/c mice aged 6 to 8 weeks were chosen because commonly used for immunology experiments and due to the reduced speckling during tissue imaging. The mice were anesthetised prior to array application with a solution of 60 µL of 25 mg/mL ketamine and 5 mg/mL xylazine in saline via intraperitoneal injection and were treated according to the protocol approved by the University of Queensland Animal Ethics Committee. Arrays were applied to the inner earlobe of the ears using an applicator device consisting of a sprung piston. Different impact velocities and energies were generated firing pistons of different masses and varying the initial spring compression through holes drilled in the cylinder housing. The mass was decreased from the standard 35 g of the brass piston, using a plastic piston jointly with ~9 g incremental weights screwed on its top end. During application, the ear rested on a 3 mm-PDMS backing slab. Adhesive carbon tabs fixed the ear to the PDMS and the PDMS to the bench support. The array was left in place for 2 min and then carefully removed. The animals were euthanized immediately after treatment through cervical dislocation and the ears excised for experimental characterization.

Example 2

Experimental Characterization of Skin Penetration

The excised ear specimen was immediately fixed by immersion into in 2% paraformaldehyde in phosphate buffer saline (PBS) for ~2 hours, and then frozen in Optimal Cutting Temperature® (OCT) compound (Tissue Tek, QLD, Australia). 10 µm-thick sections of frozen ear were sectioned normal to the skin surface and approximately parallel to projection holes rows using a Leica Ultracut UCT cryo-microtome (Leica Microsystems, Wetzlar, Germany) at the HistoTechnology facility of the QIMR Berghofer Medical Research Institute. Sections were imaged under a Zeiss LSM510 confocal microscope (Carl Zeiss Inc., Germany), using excitation and collection wavelengths of 488 nm and 500-550 nm nm, respectively. The fluorescent tracks left by fluorescent microsphere-coated projections were measured using imageJ (NIH, USA, http://imagej.nih.gov/ij/) for a minimum of 3 slides (distributed uniformly across the treated area) per ear sample, resulting in over 100 measurements per application condition. Because penetration depth varied across the array, the measurements taken for each slides were divided in an edge group, including up to 10 tracks from each side, and a center group, including all other tracks. For each slide the mean and standard deviation of the depth measurements was calculated for the edge group and center group independently. A weighted average was performed on the center group means and standard deviation for each slide within a sample, with weights equal to the number of track measured per slide. This allowed the measure to rely more on slides with a larger amount of tracks. The standard deviation was also calculated across the slides within a sample. An identical procedure was followed for the edge group. For each one of the n=4 ear samples, the mean and standard deviation between the center and edge group means gave the sample mean and error. The overall mean (across the repeats of each penetration condition) penetration depth (FIGS. 4B, 5A-5E and 6A-B) was further calculated as weighted average across sample means with weights equal to the number of tracks measured in each ear, to allow the result to rely more on samples where more tracks were measured. The standard deviation across the samples means was taken as measure of overall standard error (se) of the mean depth and plotted as error-bars (FIGS. 4B, 5A-5E and 6A-B). To quantify the penetration depth variation due to skin (and application) variability across subjects (mice), the standard deviation (of the population) was estimated by multiplying the se of the mean depth by the square root of the number of terms nt in each average step performed, according to the Bienaymé's formula se=sd/(nt)0.5 (see any inferential statistics textbook). Note that this is a rough approximation because statistical independence of the values in the sample cannot be strictly assumed. This factor is +20.5400.5 (where '2' derives from the step where center and edge means were averaged, and '40' is (conservatively) the largest number of tracks measured in an edge or center group). To quantify the penetration depth variation due to microprojection position across the array, the depths of the 10 most peripheral tracks were averaged across slides, and then again across samples. The maximum of such 10 mean depths was taken to be the upper end of the bar in FIG. 4D. Similarly, the depths of 10 center tracks were averaged across slides, and then across samples. The minimum of such 10 mean depths was taken to be the lower end of the bar in FIG. 4D. Separately, cryogenic SEM of penetrated skin was performed in accordance with Coffey et al. (J. W. Coffey, S. R. Corrie, M. A. Kendall, Biomaterials 2013, 34, 9572).

Example 3

Indenter Microprojection Model

Figure 10:
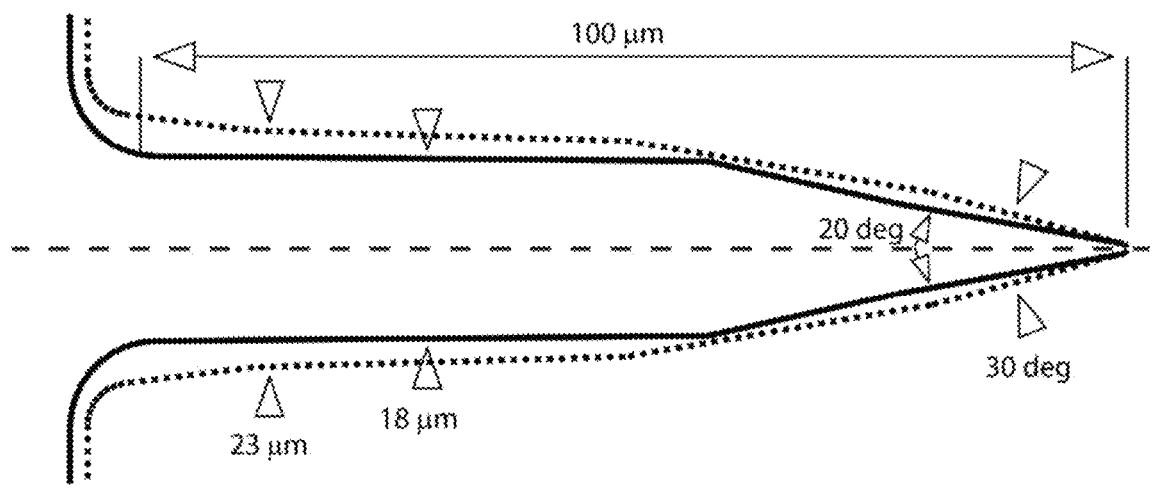
FIG. 10 is a schematic diagram of model geometry of uncoated (full) and coated (dashed) microprojection.
Figure 11A:
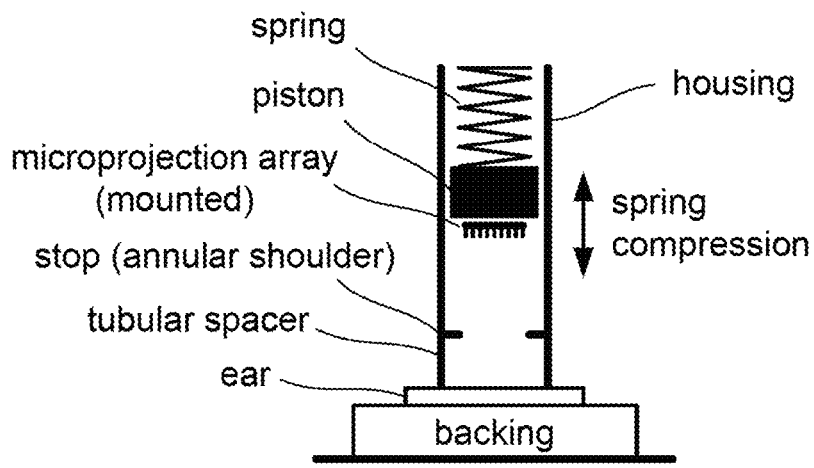
FIGS. 11A and 11B are a schematic representations of an applicator that includes a housing containing a driver, a tubular spacer that in use is positioned with an open end in contact with a surface of skin to thereby space the housing from the skin and a stop positioned proximate the open end of the spacer. The driver drives a microprojection array releasably mounted to the driver and the microprojection array is released from the driver prior to the microprojection array contacting the ear.
Figure 11B:
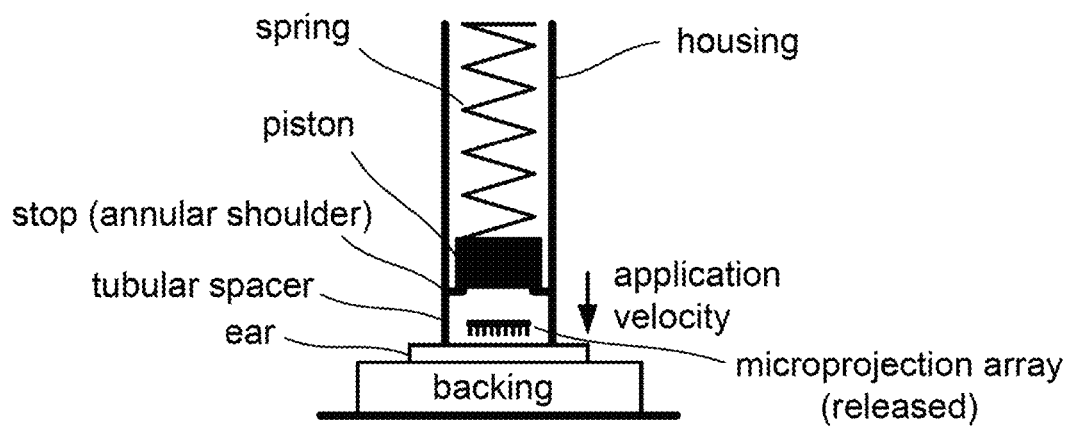

The microprojection geometry was drawn according to the SEM measurements (FIG. 10). The coated profile was considered for the penetration-depth study to accurately reproduce the characteristics of the arrays used for the experimental validation. The microprojections (or indenters) were assumed to be undeformable because silicon ($E_{Si}$>100 GPa) is over 100-fold stiffer than the skin (M. A. Hopcroft, W. D. Nix, T. W. Kenny, J Microelectromech S 2010, 19, 229). Euler buckling theory (R. C. Hibbeler, in Statics and Mechanics of Materials, Prentice Hall, Singapore 2004) was used to estimate the critical axial load of microprojections ~40 mN, which is above the maximum force acting on axially on the tip for the application conditions used in this work. Post-application examination of the arrays showed negligible or no microprojection failure.

The motion of the rigid analytical surface that modeled the projection was characterized by an initial velocity (i.e. the velocity generated by the applicator) and a bound mass (determined by the piston mass). The movement was restricted to translation along the vertical axis x=0, y=0, i.e. orthogonal indentation respect to the skin surface. Normal contact interactions were implemented in the FEA using the kinematic contact method because the penalty method was occasionally observed to allow cross-over of the master (microprojection) and slave (skin) surfaces. This happened although the skin elements in contact with the indenter/microprojection were always much smaller than the tip radius (<<0.5 µm). In contrast, the simpler penalty method was used to model tangential friction contact. A friction coefficient of 0.4 was chosen according to the experimental measurement of Bhushan and colleagues (B. Bhushan, J Colloid Interf Sci 2012, 367, 1; B. Bhushan, S. Chen, S. R. Ge, Beilstein J Nanotech 2012, 3, 731).

Example 4

FE Parameterization of Skin Fracture

Ultimate and yield strength, and plastic strain at damage were derived from previous works (R. C. Haut, Journal of Biomechanical Engineering-Transactions of the Asme 1989, 111, 136). The properties measured for the SC in high humidity conditions (~90% RH) where used to parameterize the VE, because the corneocytes are essentially flattened and dried epidermal cells. The properties measured for whole skin were used to parameterize the dermis because this layer dominates the skin overall composition and mechanical properties (R. Reihsner, B. Balogh, E. J. Menzel, Med Eng Phys 1995, 17, 304). For simulations including fracture, the vertical mesh pitch (i.e. element length) was increased in the SC and VE and decreased in the deep dermis to allow larger element deformation and better accuracy in the simulation of dermal penetration.

Example 5

Experimental Characterization of Impact Velocity and PDMS Backing Behavior

To characterize the impact response of the backing alone, the applicator was fired (n=5) without array on the PDMS+ carbon tab (no ear) using different masses and spring compressions (resulting in 1-7 m s$^{-1}$). The movement of the piston was filmed using a Photron SA4 high-speed camera (HSC) at 20,000 frames s$^{-1}$ (Photron Inc., San Diego, CA, USA). We tracked the motion of the piston with the HSC software to obtain piston displacement, velocity and acceleration over time before and after contact with PDMS. The dynamic compression displacement of the backing was then the combined with the transient impact force measured (n=5) with a quartz force sensor (model 208C02, PCB piezoelectronic, Depew, NY, USA) placed under the PDMS slab and recorded using a labview program (National Instrument Corp., Austin, TX, USA). The resulting force-displacement characteristic (FIG. 9) was non-linear with a small-strain stiffness ~20 N mm$^{-1}$. This was in agreement with dynamic mechanical analysis (DMA) tests (not shown) using an Instron Testing System 5543 (Instron, Norwood, MA, USA) equipped with a 5×5 mm$^2$ probe driven at 50 Hz with peak-to-peak amplitude of ~0.8 mm (i.e. peak displacement velocity ~0.1 m s$^{-1}$). The loss tangent was tan δ=0.23+ 0.06 and in the typical range for elastomers and viscoelastic rubbers. Separately, the impact energy U (FIG. 3H) was calculated from the momentum p=(2 Um)$^{0.5}$, which was obtained integrating the load-cell force-time curves (FIG. 8) up to the peak.

Example 6

Backing Lumped-Parameter Model

The backing was modeled as a viscoelastic material using the lumped-parameter Kelvin-Voigt-like element consisting of a mass connected to ground through a spring-damper parallel, and implemented in Abaqus using a connector element. The non-linear stiffness k measured with the impact tests (FIG. 9) was implemented in tabular form. The effective mass m* accounts for the inertia of the mass distributed across the thickness of PDMS itself, hence was approximated to ⅓ of the mass of the PDMS volume covered by the piston according to E. Linder-Ganz, A. Gefen, Mechanical compression-induced pressure sores in rat hindlimb: muscle stiffness, histology, and computational models, Vol. 96, 2004. The damping coefficient is c=tan δ (k m*)$^{0.5}$, where k was approximated to the small-strain value. This model (backing only) was employed to simulate the backing impact test and the parameterization iteratively refined until the numerical force response matched the results of the backing impact tests. All lumped parameters were scaled according to the area simulated when used in conjunction with the skin FE model, i.e. m*, k and c relative to the piston impact tests where divided by the piston cross-sectional area and multiplied by the square of the microprojection spacing.

Example 7

Figures 2A, 2B, 2C:
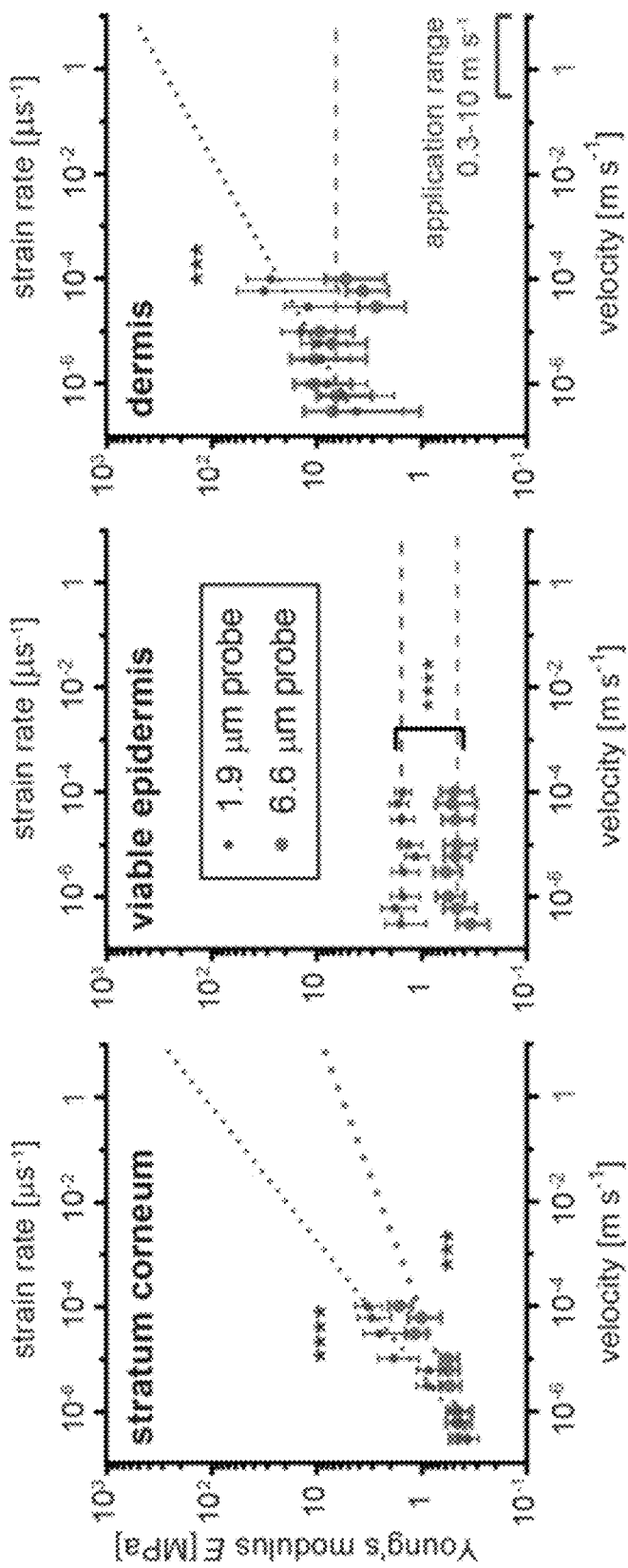
FIGS. 2A-2H are graphical representations of the hyperelastic properties for the skin layers (SC=stratum corneum, VE=viable epidermis, dermis) of mouse ear as a function of indentation velocity (or peak logarithmic strain rate)
Figures 2D, 2E, 2F:
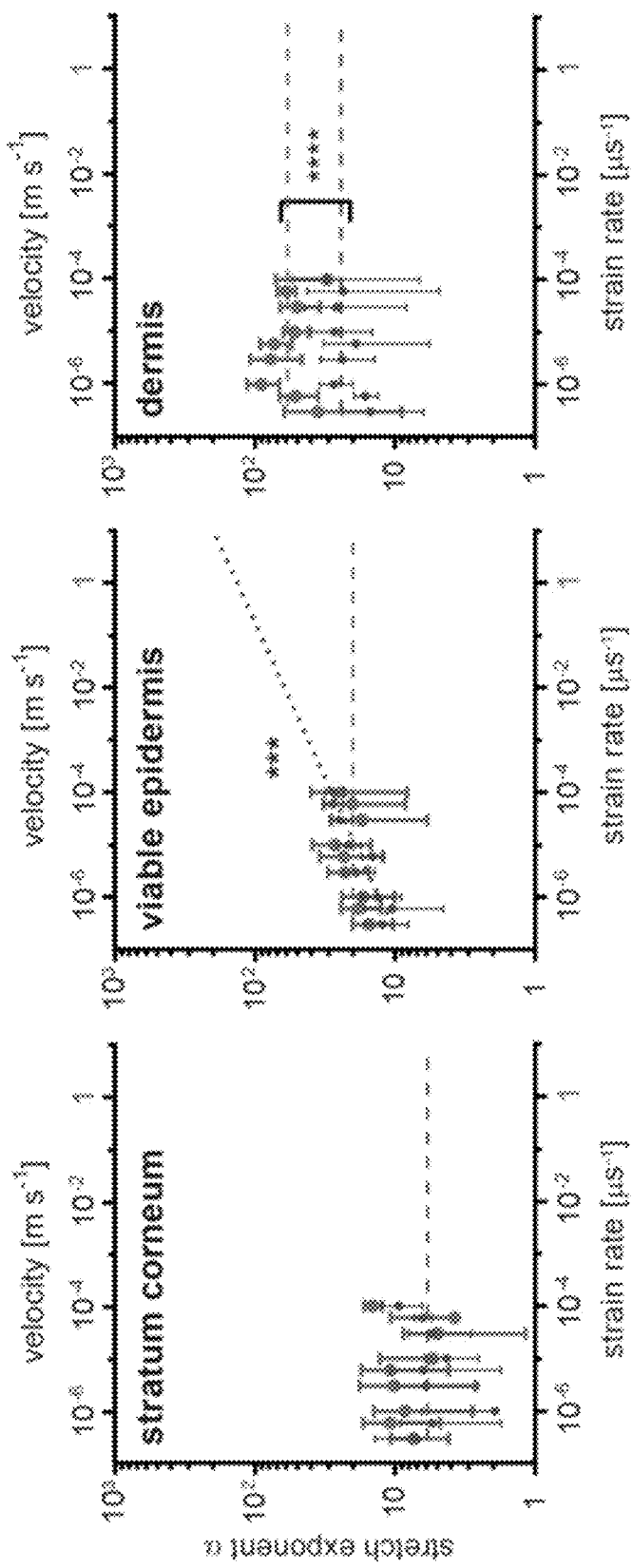
Figure 2H:
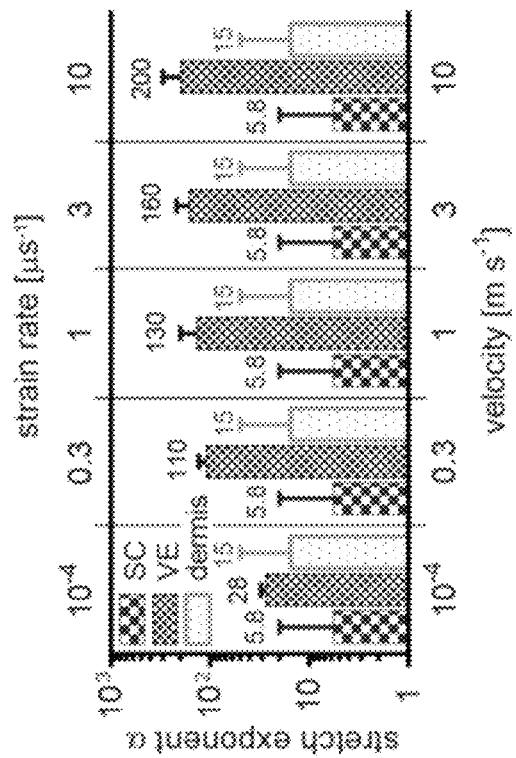
Figure 2G:
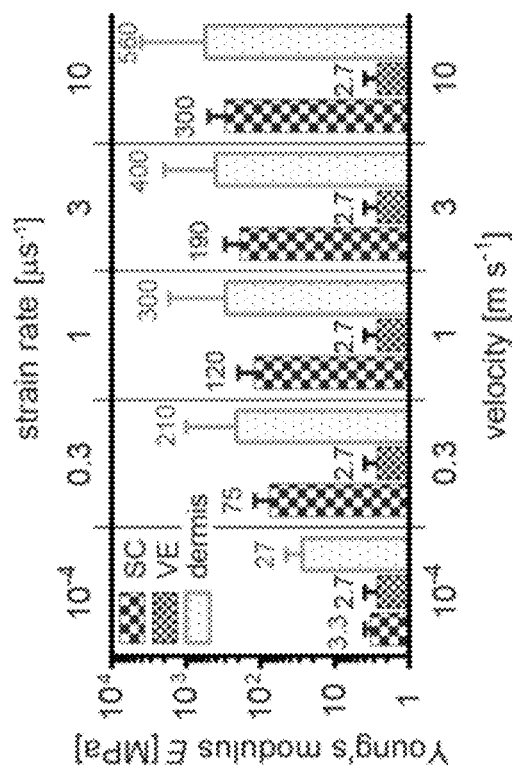

The Out-of-Plane Hyperelastic Properties of Skin Layers for Varying Strain Rates The strain-rate dependence of skin elasticity by indenting individual strata of freshly-excised mouse ear (SC, VE and dermis) with spherical tips (1.9 μm and 6.6 μm in diameter) at different velocities was investigated. This experimental procedure and the extrapolation hyperelastic 1st-order Ogden parameters was performed as described by M. L. Crichton, B. C. Donose, X. F. Chen, A. P. Raphael, H. Huang, M. A. F. Kendall, Biomaterials 2011, 32, 4670 (FIG. 2A-2F). In FIGS. 2A-2F, the purple data were collected with a 1.9 μm probe and the green data were collected with a 6.6 μm probe. The approximate logarithmic strain-rate generated is indicated by the top abscissa. A dotted line indicates that a statistically significant Spearman correlation was found between the hyperelastic parameter and the velocity/strain rate, and represents a linear regression in Log-Log scale. A horizontal dashed line indicates that the correlation was not significant (p>0.05). A square bracket indicates a statistically significant variation of the hyperelastic parameter with probe size; **p<0.0001, *p<0.001. Young's modulus E of the SC (both probe sizes; FIG. 2A) and dermis (small probe only; FIG. 2C), and the stretch exponent a of the VE (small probe only; FIG. 2E) significantly correlated (Spearman r≥0.95, p<0.001) with the indentation velocity. This further implicates correlation with the peak strain rate at contact because of its defining linear relationship with the probe impact velocity. Power relationships, i.e. the dotted straight lines in Log-Log scale, fitted these datasets better (adjusted R$^2$>0.83 except for SC 6.6 μm-probe E that scored 0.62) than logarithmic, linear and exponential curves. This rate dependency is in general agreement with the elastic properties previously extrapolated from in-plane uniaxial stretch tests on pig skin up to ~10$^{-2}$ μs$^{-1}$ [45] and rat skin up to ~10$^{-4}$ μs$^{-1}$. For the parameters that correlated with velocity non-linear regressions were used to predict the layer hyperelastic properties at larger strain rates (0.3-10 μs$^{-1}$), i.e. relevant for the application microprojection arrays (0.3-10 m s$^{-1}$). For example, FIG. 2G shows that the Young's modulus of the SC and dermis increase with strain rate and is expected to exceed 100 MPa above 1 μs$^{-1}$, whereas it remains approximately constant and below 5 MPa for the VE. FIG. 2H indicates that the stretch exponent (a) of the VE may increase over 100 at strain rate >1 μs$^{-1}$. No previous report of such effect was found for the skin. In FIGS. 2G and 2H, both the column height and the numbers indicate the means; the error bars represent the se for the experimental measurement at 10$^{-4}$ m s$^{-1}$, whereas show the 90% prediction band for the values extrapolated at 0.3-10 m s$^{-1}$. Separately, the smaller tip resulted in a statistically significant (Wilcoxon p<0.0001) larger E for the VE (FIG. 2B) and lower a for the dermis (FIG. 2F), compared to the larger tip. Recent measurements of whole mouse ear skin showed an inverse Log-Log linear trend ($E_{skin}$=29×(2r)$^{-1}$; $E_{skin}$ in MPa, r in μm) between the Young's modulus and the probe radius r across μm to mm scales. The analogous curve (not shown) intercepting our two scale-dependent values of VE Young's modulus (averaged over the velocities) was $E_{VE}$=2.7×(2r)$^{-0.9}$. SC stretch exponent did not show significant scale or rate dependence (FIG. 2D), thus the overall mean across the velocities for the small probe was reported in FIG. 2H.

Example 8

Skin Failure and Fracture Mechanics During Penetration: Model and Properties

Figure 7:
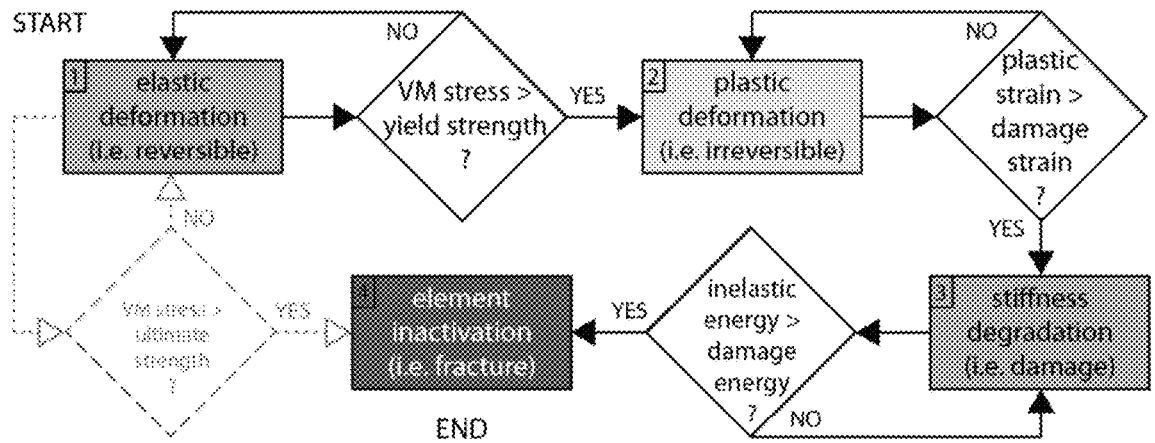
FIG. 7 is a flowchart of skin failure model, in which the clockwise flow describes the approach used in the present application; whereas the anti-clockwise flow (in grey) shows the simplified implementation used in previous work (VM=von Mises)

Characterization of skin penetration following penetrator impact was accomplished by numerically modeling microprojection application to skin and comparing against experimental observations. FIG. 7 illustrates the descriptive framework used to capture skin failure and fracture mechanics. In brief, 1) a skin element deforms reversibly according to the hyperelastic properties; 2) when the von Mises (VM) stress exceeds the yield strength, it starts deforming irreversibly (plastically) according to a linear curve (dotted) that intercepts the stress-strain coordinate defining the onset of damage (breaking strength and strain at damage); 3) when the plastic strain exceeds a damage threshold, the skin element progressively loses stiffness (material damage) linearly with the plastic energy dissipated (dashed line); 4) the element is completely inactivated when this plastic energy reaches a characteristic fracture energy.

The initial values for the failure properties were determined starting from previous skin mechanical tests and then refined to validate the fracture model against the penetration experiments. The puncture and tearing energy of whole skin and isolated SC has been reported to exceed 600 pJ $\mu m^{-2}$. Initially, simulation of a 2 m s$^{-1}$ microprojection impact using the threshold strengths and strains and fracture energy of 600 pJ $\mu m^{-2}$ for all skin layers resulted in failure initiation and plastic deformation of the elements. However, no element inactivation occurred above 6 μm displacement of the tip into the skin, with a maximum stiffness degradation <10%. This indicated that the fracture energy had been overestimated, possibly because previous measurements could not isolate fracture dissipation from other energetic contributions (e.g. elastic strain or yielding). Hence, we varied the layer fracture energies in the range 0-200 pJ $\mu m^{-2}$ (0, 0.2, 1, 6, 35, 100 and 200 pJ $\mu m^{-2}$ were used) until the simulations matched the fracture behavior observed experimentally. For example, the SC optimal energy was approximately 35 pJ $\mu m^{-2}$ suggesting that its rupture occurs through a combination of delamination (energetically 'cheaper' 1-10 pJ $\mu m^{-2}$) and tear (energetically more 'costly' ~103 pJ $\mu m^{-2}$). Using the layers optimal energies, the total irreversible strain energy (i.e. plastic and damage dissipations) when the projection has penetrated to the bottom boundary of the dermis (i.e. 4.45 μs after the contact) was about 100 nJ. The simulations showed that this value was most sensitive to the dermis fracture energy, probably due to its larger thickness. The dissipation error bounds were taken to be 50 nJ and 170 nJ, which resulted when the dermis was parameterized with 1 pJ $\mu m^{-2}$ and 35 pJ $\mu m^{-2}$, respectively. Such error range is reasonably tight compared to the total energy of the system (the application energy per projection is 21 uJ) and is satisfactory for the purpose of this work considering the limited literature about rupture energy measurements, especially for penetration-like fracture modes.

SC flaps partially overlap with the VE. This non-physical behavior occurs because, for simplicity, no 'self'-contact interaction properties were defined for the skin elements. However, the overlap involves skin portions that have already failed and have little or no load-bearing capacity; therefore, the errors in strain energy and stress were assumed to be negligible. Interestingly, stiffness degradation and fracture (element inactivation) originated ~1 μm off the microprojection axis, i.e. where the dilatational strain peaked, rather than immediately below the tip where the VM stress and compressive strain peaked. This also indicates that this fracture approach captures, at least in part, the different rupture behaviors in tension and compression, in contrast with fracture models solely based on a VM stress threshold. Note that the cartilage was not assigned failure mechanisms because this work focuses on skin targeting and cartilage penetration is avoided. Rather, to avoid bias of the numerical results due to artificial cartilage resistance to penetration, the projection was allowed to penetrate the cartilage with at zero energy cost by deactivating contact interactions of its FE nodes with the microprojections. Having established the optimal skin fracture parameters, this failure implementation is used in the next section to simulate the penetration by arrays of microprojections.

Example 9

Figures 3A, 3B, 3C, 3D:
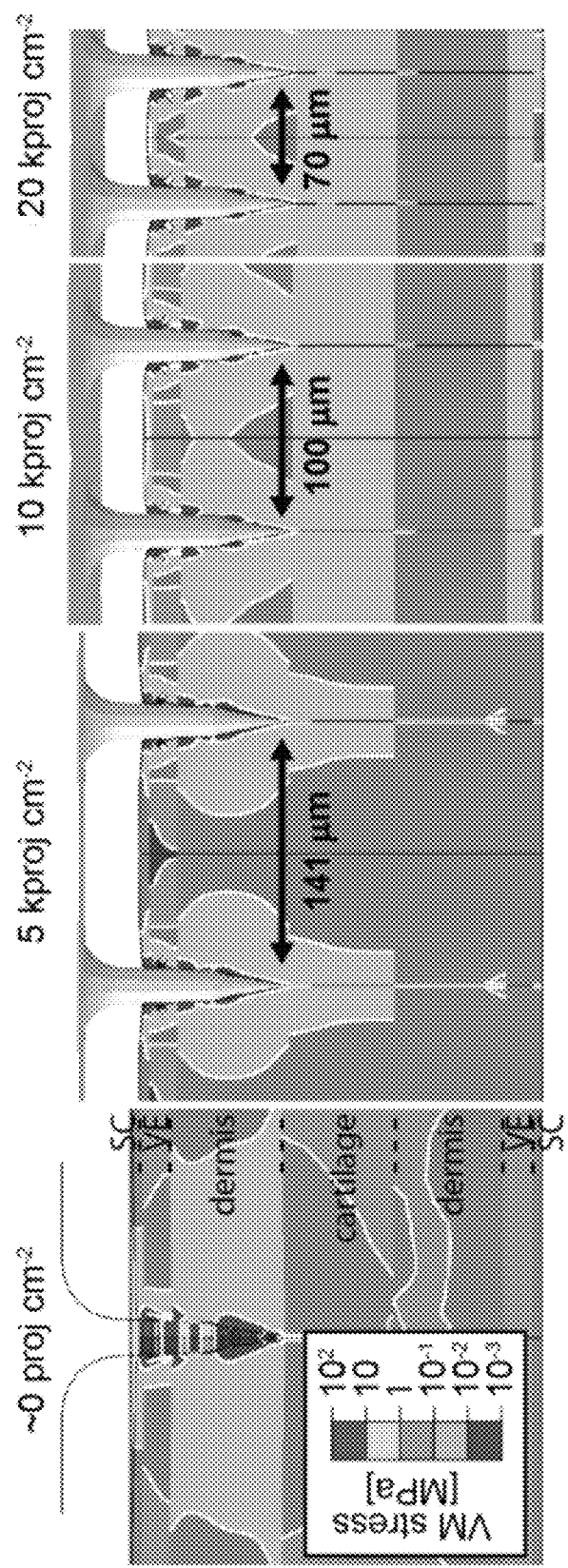
FIGS. 3A-3D are graphical representations of skin stress and energy transfers during the penetration by arrays with different densities applied with equal energy per projection (~½*35 g*(2 m s$^{-1}$)2/3000)
Figure 3E:
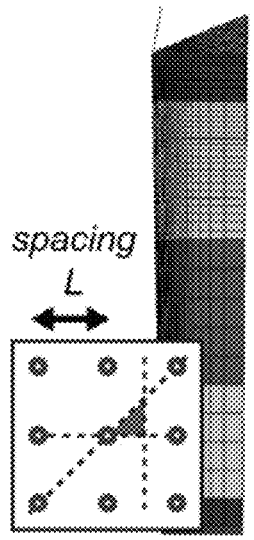
FIG. 3E is a diagram of symmetric FE geometry and mesh used to simulate the penetration of arrays with ≥5,000 proj cm$^{-2}$, in which the inset shows the fundamental skin unit simulated (red) and the planes of symmetry (dashed lines) on a top-view schematics of the array.
Figure 3F:
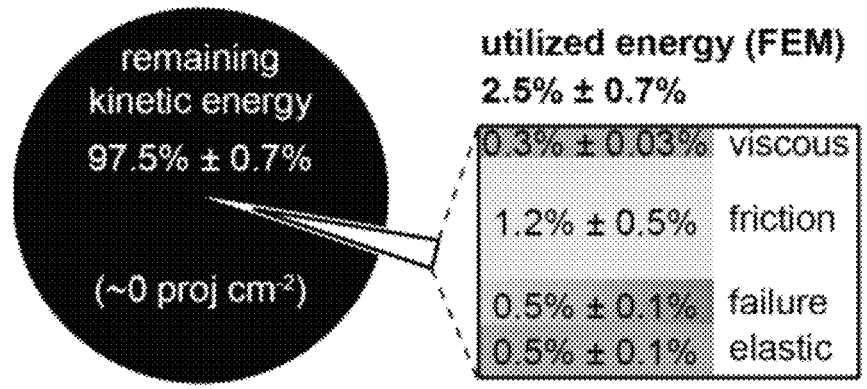
FIG. 3F is a diagram of the fraction of application energy (mean±range) utilized during the penetration of the ~0 proj cm$^{-2}$ array into mouse ear when the tip reaches the bottom of the (ventral) dermis as calculated using FEM; the range represent the variation between successive time points (+0.5 μs)
Figure 3G:
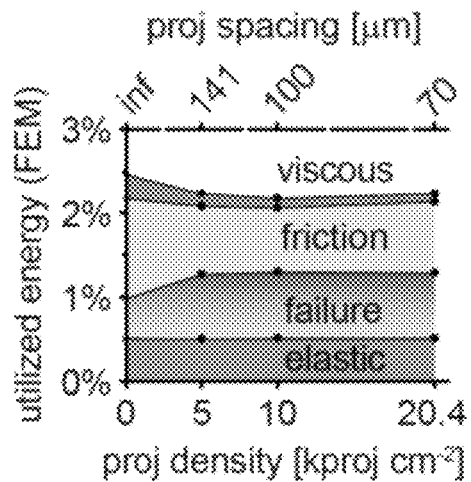
FIG. 3G is a diagram of the energy utilized as function of projection density/spacing as calculated using FEM.
Figure 3H:
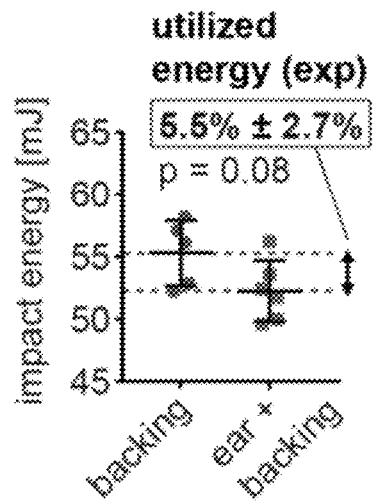
FIG. 3H is a diagram of the energy fraction (mean±sd) transferred (utilized) to the ear as measured experimentally from the difference between the impact energies transmitted across the backing and the ear+backing to an underlying force sensor. FEM=finite-element modeling, exp=experiment, inf=infinite.
Figure 8:
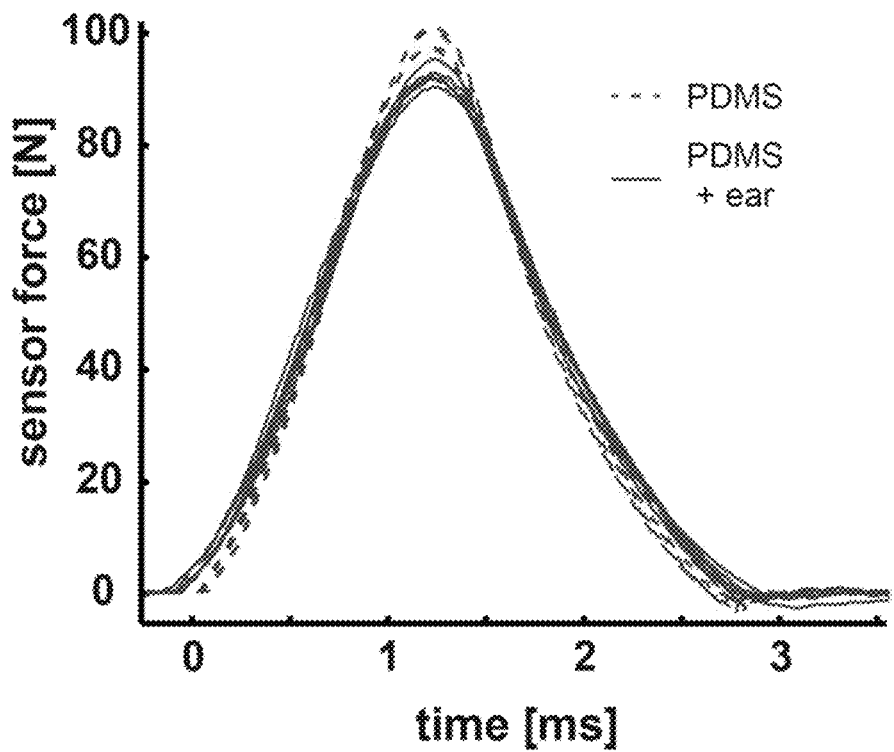
FIG. 8 is a plot of force measured by piezoelectric load cell placed under the PDMS following ~2 m s$^{-1}$ impact of a microprojection array on the PDMS-backed skin ('PDMS+ear') and flat patch on PDMS backing only ('PDMS')
Figure 9:
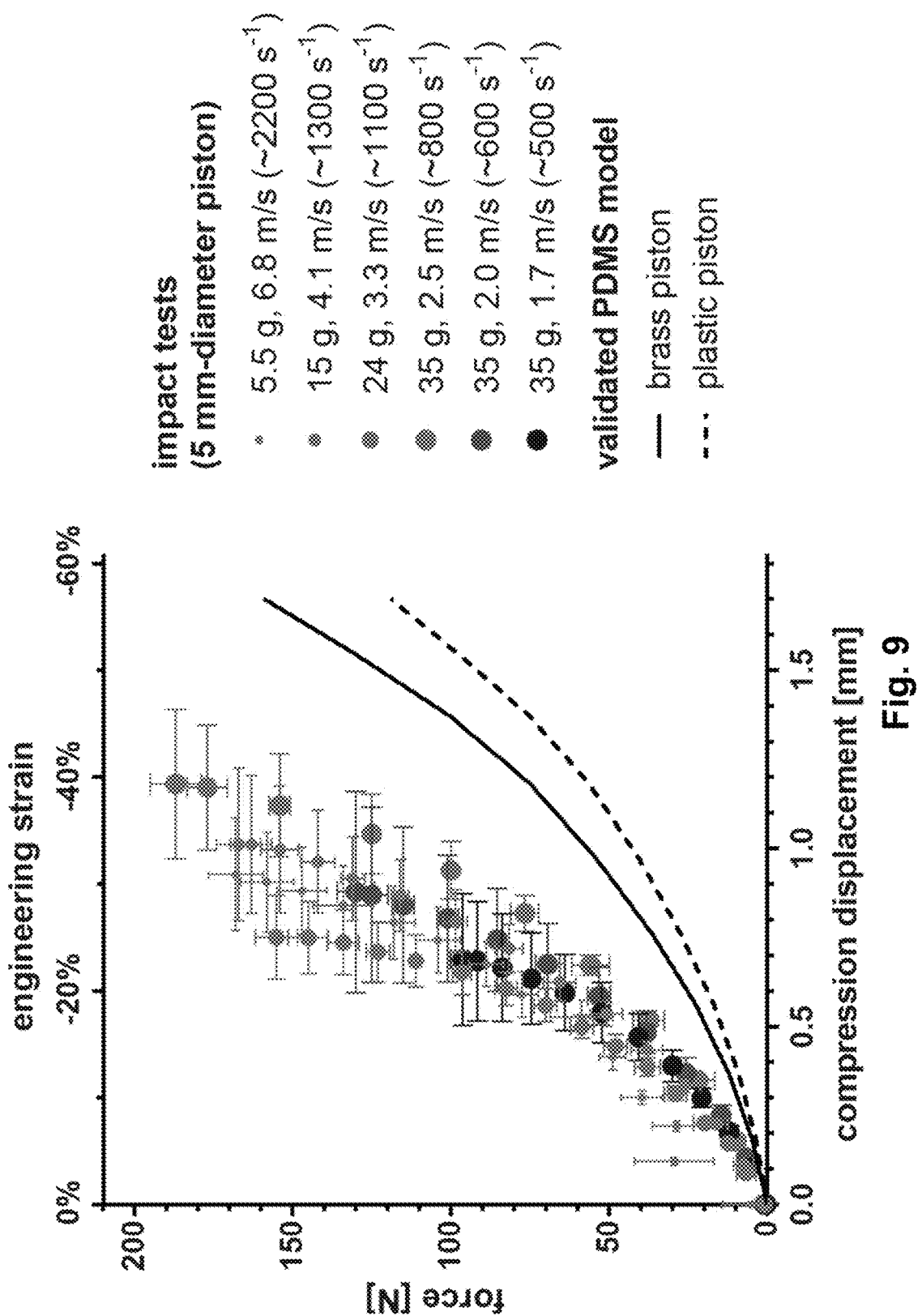
FIG. 9 is a plot of force versus compression displacement for impact tests that were performed on carbon tab-topped PDMS firing a 5 mm-diameter flat-ended piston; piston mass and impact velocity (and relative theoretical peak engineering strain rate) are indicated; the green datasets have ~constant kinetic energy; the vertical error-bars indicate the sd of the measurements across the different PDMS samples; the horizontal error-bars of the impact tests show the uncertainty (sd over the different PDMS samples) of the compression displacement measures using the high-speed camera; and the full and dashed lines show the stiffness curves selected after PDMS model validation for the brass and plastic pistons, respectively.

Energy Contributions to Skin Penetration: Elastic Deformation, Fracture and the Role of Subcutaneous Backing Layers FIG. 3A represents a snapshot along the penetration trajectory of a ~3000-microprojection array impacting the skin at 2 m s$^{-1}$ with a bound mass (applicator piston) of ~35 g. According to this simulation, when a microprojection has penetrated to the dermis bottom boundary its velocity has decreased negligibly (<2%) and penetration would continue across the cartilage. FIG. 3F shows that less than 3% of the initial application energy is transferred to the skin, while the majority remains array kinetic energy. In contrast, experiments showed that similar application velocities (~2 ms$^{-1}$) result in mid- to deep-dermal penetration. This means that the current model does not account for several mechanisms that absorb a major fraction (>90%) of the application energy. One possible reason could be attributed to the linked assumption that microprojections are largely spaced and do not influence each other. Hence, the penetration of arrays with finite microprojection densities/spacings (FIG. 3B-D) was simulated using the 3D symmetric FE geometry schematized in FIG. 3E. Interestingly, densities around 10 kproj cm$^{-2}$ (i.e. 10,000 proj cm$^{-2}$) appeared to decrease the friction dissipation in favor of an increased energy contribution to failure and fracture (FIG. 3G). The elastic strain energy was approximately constant with the projection density; however, VM stress above 1 MPa concentrates at the penetration site in the ventral (top) skin layers when the projections are largely spaced, while it progressively spreads to the cartilage, dorsal (bottom) dermis, VE and SC as the density approaches 20 kproj cm$^{-2}$. Most importantly, the total energy transferred to the skin when the projection has penetrated to the bottom of the dermis is essentially independent of the microprojection density (at least up to 20 kproj cm$^{-2}$). Rather, the remaining kinetic energy may be transferred to the backing layer, i.e. a 3 mm-thick PDMS slab placed under the ear during the microprojection array application. This is employed to cushion the impact and avoid ear tissue damage while allowing applications at high velocities (~m s$^{-1}$). The force transmitted across the backing was measured by placing a piezoelectric load cell below the PDMS slab (i.e. on the bench support; FIG. 8). FIG. 3H shows that this energy is approximately 5% lower than the energy transmitted when a flat (projection-less) patch is applied on the backing alone (without mouse ear). This means that only a small amount of energy (~5%) is transferred to the ear, which explains the excess of energy in the simulation (~95% to the backing). Hence, accurate modeling of skin penetration requires accounting for possible compliant backing layers like our PDMS or subcutaneous fat and muscle found in vivo (less stiff than skin).

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. An apparatus for delivering an active ingredient into skin of an animal at a defined depth, the apparatus including:
   a) a microprojection array including a plurality of microprojections; and,
   b) an applicator comprising a driver, wherein the driver is releasably attached to the microprojection array for driving the microprojection array towards the skin at a driver velocity in use so that the microprojection array separates from the driver prior to the microprojection array impacting the skin and the microprojection array impacts on the skin with a mass-to-velocity ratio of between 0.005 g/m/s and 0.1 g/m/s, wherein the mass is a mass impacting the skin, wherein the mass impacting the skin is only a mass of the microprojection array.

2. The apparatus of claim 1, wherein the mass of the microprojection array is between 0.1 g and 1.0 g.

3. The apparatus of claim 1, wherein the microprojection array is configured to impacts the skin at velocities between 20 m/s and 30 m/s.

4. The apparatus of claim 1, wherein the microprojection array has an area between 10 mm$^2$ and 40 mm$^2$.

5. The apparatus of claim 1, wherein the plurality of microprojections are solid.

6. The apparatus of claim 1, wherein the plurality of microprojections have a length of between 200 μm and 300 μm.

7. The apparatus of claim 6, wherein the plurality of microprojections include:
   a) a base having a width of about 5 μm to about 50 μm; and,
   b) a tip having a width of 0.5 μm to 2 μm.

8. The apparatus of claim 7, wherein the base has two substantially parallel sides with a draught angle of 1 to 20 degrees up to a transition point where the draught angle becomes from 20 to 70 degrees.

9. The apparatus of claim 1, wherein the driver abuts against a stop which is configured to thereby release the microprojection array from the driver.

10. The apparatus of claim 9, wherein the stop includes an annular shoulder.

11. The apparatus of claim 9, wherein the applicator includes:
    a) a housing containing the driver; and,
    b) a substantially tubular spacer that in use is positioned with an open end in contact with a surface of the skin to thereby space the housing from the skin, the stop being provided proximate the open end of the spacer.

12. The apparatus of claim 1, wherein the driver is configured to be urged from a retracted position to an extended position using a biasing mechanism, and wherein the biasing mechanism and engagement between the driver and a housing define a driver velocity in use.

13. The apparatus of claim 12, wherein the driver is a piston.

14. The apparatus of claim 13, wherein the engagement is frictional engagement between the piston and a piston chamber within the housing.

15. The apparatus of claim 12, wherein the biasing mechanism is a pneumatic actuator.

16. The apparatus of claim 1, wherein the microprojection array is configured to impact on the skin with the mass-to-velocity ratio sufficiently high to dissipate inertia so as to avoid mechanical stress on body parts underlying the skin and cause a controlled amount of mechanical stress for immune-enhancing inflammation.

17. The apparatus of claim 1, wherein at least a tip of each microprojection of the plurality of microprojections is coated.

18. The apparatus of claim 1, wherein the active ingredient is one or more vaccine antigens.

* * * * *

UNITED STATES PATENT AND TRADEMARK OFFICE
CERTIFICATE OF CORRECTION

Page 1 of 1

PATENT NO. : 12,090,295 B2
APPLICATION NO. : 17/241927
DATED : September 17, 2024
INVENTOR(S) : Stefano Meliga et al.

It is certified that error appears in the above-identified patent and that said Letters Patent is hereby corrected as shown below:

In the Claims

Column 23, Claim 3, Line 25:
"to impacts the skin" should read: --to impact the skin--.

Column 24, Claim 12, Line 20:
"define a driver" should read: --define the driver--.

Signed and Sealed this
Third Day of December, 2024

Katherine Kelly Vidal
*Director of the United States Patent and Trademark Office*